United States Patent [19]
Lehmann

[11] Patent Number: 6,153,418
[45] Date of Patent: Nov. 28, 2000

[54] CONSENSUS PHYTASES

[75] Inventor: Martin Lehmann, Inzlingen, Germany

[73] Assignee: Roche Vitamins Inc., Parsippany, N.J.

[21] Appl. No.: 09/121,425

[22] Filed: Jul. 23, 1998

[30] Foreign Application Priority Data

Jul. 24, 1997 [EP] European Pat. Off. .............. 97112688

[51] Int. Cl.$^7$ ............................... C12N 9/16; C12N 9/14; A61K 38/43; A61K 38/53
[52] U.S. Cl. ........................ 435/195; 435/196; 424/94.1; 424/94.6
[58] Field of Search ................................... 435/195, 196; 424/94.1, 94.6

[56] References Cited

U.S. PATENT DOCUMENTS

| | | | |
|---|---|---|---|
| 5,436,156 | 7/1995 | Van Gorcom et al. | 435/252.3 |
| 5,863,533 | 1/1999 | Van Gorcom et al. | 435/94.6 |

FOREIGN PATENT DOCUMENTS

| | | |
|---|---|---|
| 420 358 | 4/1991 | European Pat. Off. . |
| 0 299 108 | 5/1994 | European Pat. Off. . |
| 0 619 369 A1 | 10/1994 | European Pat. Off. . |
| 684 313 | 11/1995 | European Pat. Off. . |
| 747 483 | 12/1996 | European Pat. Off. . |
| 235478 | 9/1990 | New Zealand . |
| 93/16175 | 8/1993 | WIPO . |
| 94/03072 | 2/1994 | WIPO . |
| 94/03612 | 2/1994 | WIPO . |

OTHER PUBLICATIONS

Shieh and Ware, Appl. Microbiol. vol. 16, pp. 1348–1351 (1968).
Janecek, S., Process Biochem. vol. 28, pp. 435–445 (1993).
Fersht, A. R. & Serrano, L., Curr. Opin. Struct. Biol. vol. 3, pp. 75–83 (1993).
Alber, T., Annu. Rev. Biochem. vol. 58, pp. 765–798 (1989).
Matthews, B.W. Biochemistry vol. 26, pp. 6885–6888 (1987).
Matthews, B. W., Curr. Opin. Struct. Biol. vol. 1, pp. 17–21 (1991).
Pen et al., Bio/Technology vol. 11, pp. 811–814 (1994).
Stuber et al, Immunological Methods, eds. Lefkovits and Pernis, Academic Press Inc. vol. IV, pp. 121–152 (1990).
Serrano, L. et al., J. Mol. Biol, vol. 223 pp. 305–312 (1993).
Steipe B. et al., J. Mol. Biol. vol. 240 pp. 188–192 (1994).
Dox et al., J. Biol. Chem., vol. 10, pp. 183–186 (1911).
Howson et al., Enzyme Microb. Technol., vol. 5, pp. 377–382 (1983).
Lambrechts et al., Biotech. Lett., vol. 14, No. 1, pp. 61–66 (1992).
Van Hartingsveldt et al., Gene, vol. 127, pp. 87–94 (1993).
Piddington et al., Gene, vol. 133, pp. 55–62 (1993).
Kraulis, P. J., J. Appl. Cryst, vol. 24, pp. 946–950 (1991).
Merrit et al., Acta Cryst., pp. 869–873 (1994).
Wodzinzki et al., Advances in Applied Microbiology, vol. 42, pp. 263–303 (1996).

Mitchell et al., Microbiology, vol. 143, pp. 245–252 (1997).
Kostrewa et al., Nature Structural Biology, vol. 4, No. 3, pp. 185–190 (1997).
Simons et al., Br. J. Nutr., vol. 64, pp. 525–540 (1990).
Schöner et al., J. Anim. Physiol. a. Anim. Nutr., vol. 66, pp. 248–255 (1991).
Jongbloed et al., J. Anim. Sci., vol. 70, pp. 1159–1168 (1992).
Perney et al., Poultry Sci., vol. 72, pp. 2106–2114 (1993).
Farrell et al., J. Anim. Physiol. a. Anim. Nutr., vol. 69, pp. 278–283 (1993).
Broz et al., Br. Poultry Sci., vol. 35, pp. 273–280 (1994).
Dungelhoef et al., Animal Feed Sci. & Technol., vol. 49, pp. 1–10 (1994).
Piccotti et al., J. Immunol., vol. 158, pp. 643–648 (1997).
Presentation by Dr. Luis Pasamontes at the Institute of Med. Microbiologie, Basel, Switzerland, Feb. 11, 1997.
Mullaney, et al., Appl. Microbiol Biotechnol., vol. 35, pp. 611–614 (1991).
Conneely O.M., Biotechnology in the Feed Industry, T.P. Lyons (ed.), Alltech Technical Publications, pp. 57–66 (1992).
R.F. Doolitle, et al., The Proteins, Neurath, et al. editors, Academic Press, New York, p. 14 (1979).
Nunes C. S., Biol. Abstr., vol. 98 Ref. No. 126043 (1994).
Segueilha, et al., J. Fermentation and Bioeng., vol. 74 (1), pp. 7–11 (1992).
Yamada et al., Agr. Biol. Chem., vol. 32 (10), pp. 1275–1282 (1968).
Lee, et al., Science, vol. 239, pp. 1288–1291 (1988).
Yamamoto et al., Agr. Biol. Chem., vol. 36 (12), pp. 2097–2103 (1972).

*Primary Examiner*—Ponnathapu Achutamurthy
*Assistant Examiner*—Peter P. Tung
*Attorney, Agent, or Firm*—Mark E. Waddell; Stephen M. Haracz; Bryan Cave LLP

[57] ABSTRACT

A process for obtaining a consensus protein from a group of amino acid sequences of a defined protein family, proteins and polynucleotides so obtained, and compositions containing such proteins.

11 Claims, 25 Drawing Sheets

Figure 1/1

```
                                1                                      50
A. terreus 9A-1         KhsDCNSVDh GYQCFPELSH kWGlYAPYFS LQDESPFPlD
VPEDChITFV A. terreus cbs          NhsDCTSVDr GYQCFPELSH kWGlYAPYFS LQDESPFPlD
VPDDChITFV A. niger var. awamori   NqsTCDTVDQ GYQCFSETSH LWGQYAPFFS LANESAISPD
VPAGCrVTFA A. niger T213           NqsSCDTVDQ GYQCFSETSH LWGQYAPFFS LANESVISPD
VPAGCrVTFA A. niger NRRL3135       NqsSCDTVDQ GYQCFSETSH LWGQYAPFFS LANESVISPE
VPAGCrVTFA A. fumigatus 13073      GSkSCDTVDl GYQCsPATSH LWGQYSPFFS LEDElSVSSK
LPKDCrITLV A. fumigatus 32722      GSkSCDTVDl GYQCsPATSH LWGQYSPFFS LEDElSVSSK
LPKDCrITLV A. fumigatus 58128      GSkSCDTVDl GYQCsPATSH LWGQYSPFFS LEDElSVSSK
LPKDCrITLV A. fumigatus 26906      GSkSCDTVDl GYQCsPATSH LWGQYSPFFS LEDElSVSSK
LPKDCrITLV A. fumigatus 32239      GSkACDTVEl GYQCsPGTSH LWGQYSPFFS LEDElSVSSD
LPKDCrVTFV A. nidulans             QNHSCNTADG GYQCFPNVSH VWGQYSPYFS IEQESAISeD
VPHGCeVTFV T. thermophilus         DSHSCNTVEG GYQCrPEISH sWGQYSPFFS LADQSEISPD
VPQNCkITFV M. thermophila          ESRPCDTpDl GFQCgTAISH FWGQYSPYFS VpSElDaS..
IPDDCeVTFA
```

Figure 1/2

```
Consensus              NSHSCDTVDG GYQCFPEISH LWGQYSPYFS LEDESAISPD
VPDDC-VTFV Consensus phytase      NSHSCDTVDG GYQCFPEISH LWGQYSPYFS LEDESAISPD
VPDDCRVTFV
```

```
                                  51
                                                                          100
A. terreus 9A-1         QVLARHGARs PThSKtKAYA AtIAAIQKSA TaFpGKYAFL
QSYNYSLDSE A. terreus cbs          QVLARHGARs PTDSKtKAYA AtIAAIQKNA TaLpGKYAFL
KSYNYSMGSE A. niger var. awamori   QVLSRHGARY PTESKgKkYS ALIEEIQQNV TtFDGKYAFL
KTYNYSLGAD A. niger T213           QVLSRHGARY PTESKgKkYS ALIEEIQQNV TtFDGKYAFL
KTYNYSLGAD A. niger NRRL3135       QVLSRHGARY PTDSKgKkYS ALIEEIQQNA TtFDGKYAFL
KTYNYSLGAD A. fumigatus 13073      QVLSRHGARY PTSSKsKkYK kLVTAIQaNA TdFKGKFAFL
KTYNYTLGAD A. fumigatus 32722      QVLSRHGARY PTSSKsKkYK kLVTAIQaNA TdFKGKFAFL
KTYNYTLGAD A. fumigatus 58128      QVLSRHGARY PTSSKsKkYK kLVTAIQaNA TdFKGKFAFL
KTYNYTLGAD A. fumigatus 26906      QVLSRHGARY PTSSKsKkYK kLVTAIQaNA TdFKGKFAFL
KTYNYTLGAD A. fumigatus 32239      QVLSRHGARY PTASKsKkYK kLVTAIQKNA TeFKGKFAFL
ETYNYTLGAD
```

Figure 1/3

| | |
|---|---|
| A. nidulans | QVLSRHGARY PTESKsKAYS GLIEAIQKNA TsFwGQYAFL |
| ESYNYTLGAD | |
| T. thermophilus | QLLSRHGARY PTSSKtElYS QLISrIQKTA TaYKGyYAFL |
| KDYrYqLGAN | |
| M. thermophila | QVLSRHGARa PTlKRaaSYv DLIDrIHhGA IsYgPgYEFL |
| RTYDYTLGAD | |
| | |
| Consensus | QVLSRHGARY PTSSK-KAYS ALIEAIQKNA T-FKGKYAFL |
| KTYNYTLGAD | |
| Consensus phytase | QVLSRHGARY PTSSKSKAYS ALIEAIQKNA TAFKGKYAFL |
| KTYNYTLGAD | |

101

150

| | |
|---|---|
| A. terreus 9A-1 | ELTPFGrNQL rDlGaQFYeR YNALTRhInP FVRATDASRV |
| hESAEKFVEG | |
| A. terreus cbs | NLTPFGrNQL qDlGaQFYRR YDTLTRhInP FVRAADSSRV |
| hESAEKFVEG | |
| A. niger var. awamori | DLTPFGEQEL VNSGIKFYQR YESLTRNIIP FIRSSGSSRV |
| IASGEKFIEG | |
| A. niger T213 | DLTPFGEQEL VNSGIKFYQR YESLTRNIIP FIRSSGSSRV |
| IASGEKFIEG | |
| A. niger NRRL3135 | DLTPFGEQEL VNSGIKFYQR YESLTRNIVP FIRSSGSSRV |
| IASGKKFIEG | |
| A. fumigatus 13073 | DLTPFGEQQL VNSGIKFYQR YKALARSVVP FIRASGSDRV |
| IASGEKFIEG | |
| A. fumigatus 32722 | DLTPFGEQQL VNSGIKFYQR YKALARSVVP FIRASGSDRV |
| IASGEKFIEG | |

Figure 1/4

| | | | | |
|---|---|---|---|---|
| A. fumigatus 58128 | DLTPFGEQQL | VNSGIKFYQR | YKALARSVVP | FIRASGSDRV |
| IASGEKFIEG | | | | |
| A. fumigatus 26906 | DLTAFGEQQL | VNSGIKFYQR | YKALARSVVP | FIRASGSDRV |
| IASGEKFIEG | | | | |
| A. fumigatus 32239 | DLTPFGEQQM | VNSGIKFYQK | YKALAgSVVP | FIRSSGSDRV |
| IASGEKFIEG | | | | |
| A. nidulans | DLTiFGENQM | VDSGaKFYRR | YKNLARKnTP | FIRASGSDRV |
| VASAEKFING | | | | |
| T. thermophilus | DLTPFGENQM | IQlGIKFYnH | YKSLARNaVP | FVRCSGSDRV |
| IASGrlFIEG | | | | |
| M. thermophila | ELTRtGQQQM | VNSGIKFYRR | YRALARKsIP | FVRTAGqDRV |
| VhSAENFTQG | | | | |
| | | | | |
| Consensus | DLTPFGENQM | VNSGIKFYRR | YKALARK-VP | FVRASGSDRV |
| IASAEKFIEG | | | | |
| Consensus phytase | DLTPFGENQM | VNSGIKFYRR | YKALARKIVP | FIRASGSDRV |
| IASAEKFIEG | | | | |

Figure 1/5

```
                          151                                              200
A. terreus 9A-1         FQTARqDDHh ANpHQPSPrV DVaIPEGSAY NNTLEHSlCT AFES...STV
A. terreus cbs          FQNARqGDPh ANpHQPSPrV DVVIPEGTAY NNTLEHSICT AFEA...STV
A. niger var. awamori   FQSTKLkDPr AqpgQSSPkI DVVISEASSs NNTLDPGTCT VFED...SEL
A. niger T213           FQSTKLkDPr AqpgQSSPkI DVVISEASSs NNTLDPGTCT VFED...SEL
A. niger NRRL3135       FQSTKLkDPr AqpgQSSPkI DVVISEASSs NNTLDPGTCT VFED...SEL
A. fumigatus 13073      FQqAKLADPG A.TNRAAPAI SVIIPESETF NNTLDHGVCT kFEA...SQL
A. fumigatus 32722      FQqAKLADPG A.TNRAAPAI SVIIPESETF NNTLDHGVCT kFEA...SQL
A. fumigatus 58128      FQqAKLADPG A.TNRAAPAI SVIIPESETF NNTLDHGVCT kFEA...SQL
A. fumigatus 26906      FQqAKLADPG A.TNRAAPAI SVIIPESETF NNTLDHGVCT kFEA...SQL
A. fumigatus 32239      FQqANVADPG A.TNRAAPVI SVIIPESETY NNTLDHSVCT NFEA...SEL
A. nidulans             FRKAQLhDHG S..gQATPVV NVIIPEiDGF NNTLDHSTCV SFEN...DEr
T. thermophilus         FQSAKVlDPh SDkHDAPPTI NVIIeEGPSY NNTLDtGSCP VFED...SSg
M. thermophila          FHSAlLADRG STvRPTlPyd mVVIPETAGa NNTLHNDlCT AFEEgpySTI
```

Figure 1/6

| | |
|---|---|
| Consensus AFED---SEL | FQSAKLADPG S-PHQASPVI NVIIPEGSGY NNTLDHGTCT |
| Consensus phytase AFED...SEL | FQSAKLADPG SQPHQASPVI DVIIPEGSGY NNTLDHGTCT |

201                                                    250

| | |
|---|---|
| A. terreus 9A-1 CPFETVSlTD | GDDAvANFTA VFAPAIaQRL EADLPGVqLS TDDVVnLMAM |
| A. terreus cbs CPFETVSlTD | GDAAADNFTA VFAPAIakRL EADLPGVqLS ADDVVnLMAM |
| A. niger var. awamori CSFDTIStST | ADTVEANFTA TFAPSIRQRL ENDLSGVTLT DTEVTyLMDM |
| A. niger T213 CSFDTIStST | ADTVEANFTA TFAPSIRQRL ENDLSGVTLT DTEVTyLMDM |
| A. niger NRRL3135 CSFDTIStST | ADTVEANFTA TFVPSIRQRL ENDLSGVTLT DTEVTyLMDM |
| A. fumigatus 13073 CSFDTVARTS | GDEVAANFTA lFAPDIRARa EkHLPGVTLT DEDVVsLMDM |
| A. fumigatus 32722 CSFDTVARTS | GDEVAANFTA lFAPDIRARa EkHLPGVTLT DEDVVsLMDM |
| A. fumigatus 58128 CSFDTVARTS | GDEVAANFTA lFAPDIRARa EkHLPGVTLT DEDVVsLMDM |
| A. fumigatus 26906 CSFDTVARTS | GDEVAANFTA lFAPDIRARa KkHLPGVTLT DEDVVsLMDM |
| A. fumigatus 32239 CSFDTVARTA | GDEVEANFTA lFAPAIRARI EkHLPGVqLT DDDVVsLMDM |

Figure 1/7

| | |
|---|---|
| *A. nidulans* CSFDTMARTA | ADEiEANFTA IMGPPIRkRL ENDLPGIKLT NENVIyLMDM |
| *T. thermophilus* CPFETLARNh | GHDAQEKFAk qFAPAIlEKI KDHLPGVDLA vSDVpyLMDL |
| *M. thermophila* CPFETVAsSS | GDDAQDTYlS TFAGPItARV NANLPGANLT DADTVaLMDL |
| Consensus CPFETVARTS | GDDAEANFTA TFAPAIRARL EADLPGVTLT DEDVV-LMDM |
| Consensus phytase CPFETVARTS | GDDVEANFTA LFAPAIRARL EADLPGVTLT DEDVVYLMDM |

251                                                                      300

| | |
|---|---|
| *A. terreus* 9A-1 YGYGGGNPLG | ......... ...DAhTLSPFC DLFTAtEWtq YNYLlSLDKY |
| *A. terreus* cbs YGYGGGNPLG | ......... ...DAhTLSPFC DLFTAaEWtq YNYLlSLDKY |
| *A. niger* var. awamori YGHGAGNPLG | ......... ...vDTKLSPFC DLFTHdEWih YDYLQSLkKY |
| *A. niger* T213 YGHGAGNPLG | ......... ...vDTKLSPFC DLFTHdEWih YDYLRSLkKY |
| *A. niger* NRRL3135 YGHGAGNPLG | ......... ...vDTKLSPFC DLFTHdEWin YDYLQSLkKY |
| *A. fumigatus* 13073 YGYGAGNPLG | ......... ...DASQLSPFC QLFTHnEWkk YNYLQSLGKY |
| *A. fumigatus* 32722 YGYGAGNPLG | ......... ...DASQLSPFC QLFTHnEWkk YNYLQSLGKY |

Figure 1/8

```
A. fumigatus 58128    ........ ...DASQLSPFC QLFTHnEWkk YNYLQSLGKY
YGYGAGNPLG A. fumigatus 26906    ........ ...DASQLSPFC QLFTHnEWkk YNYLQSLGKY
YGYGAGNPLG A. fumigatus 32239    ........ ...DASELSPFC AIFTHnEWkk YDYLQSLGKY
YGYGAGNPLG A. nidulans           ........ ...HGTELSPFC AIFTEkEWlq YDYLQSLSKY
YGYGAGSPLG T. thermophilus       ........ ...TDT.LSPFC ALsTQeEWqa YDYYQSLGKY
YGnGGGNPLG M. thermophila        sdpatadagg gNGrpLSPFC rLFSEsEWra YDYLQSVGKW
YGYGPGNPLG Consensus             ---------- -DATELSPFC ALFTE-EW-- YDYLQSLGKY
YGYGAGNPLG Consensus phytase     .......... .DATELSPFC ALFTHDEWRQ YDYLQSLGKY
YGYGAGNPLG
```

Figure 1/9

```
                             301                                            350
A. terreus 9A-1         PVQGVGWaNE LMARLTRAPV HDHTCVNNTL DASPATFPLN ATLYADFSHD
A. terreus cbs          PVQGVGWaNE LIARLTRSPV HDHTCVNNTL DANPATFPLN ATLYADFSHD
A. niger var. awamori   PTQGVGYaNE LIARLTHSPV HDDTSSNHTL DSNPATFPLN STLYADFSHD
A. niger T213           PTQGVGYaNE LIARLTHSPV HDDTSSNHTL DSNPATFPLN STLYADFSHD
A. niger NRRL3135       PTQGVGYaNE LIARLTHSPV HDDTSSNHTL DSSPATFPLN STLYADFSHD
A. fumigatus 13073      PAQGIGFtNE LIARLTRSPV QDHTSTNsTL vSNPATFPLN ATMYVDFSHD
A. fumigatus 32722      PAQGIGFtNE LIARLTRSPV QDHTSTNsTL vSNPATFPLN ATMYVDFSHD
A. fumigatus 58128      PAQGIGFtNE LIARLTRSPV QDHTSTNsTL vSNPATFPLN ATMYVDFSHD
A. fumigatus 26906      PAQGIGFtNE LIARLTRSPV QDHTSTNsTL vSNPATFPLN ATMYVDFSHD
A. fumigatus 32239      PAQGIGFtNE LIARLTNSPV QDHTSTNsTL DSDPATFPLN ATIYVDFSHD
A. nidulans             PAQGIGFtNE LIARLTQSPV QDNTSTNHTL DSNPATFPLD rKLYADFSHD
T. thermophilus         PAQGVGFvNE LIARMTHSPV QDYTTVNHTL DSNPATFPLN ATLYADFSHD
M. thermophila          PTQGVGFvNE LLARLAgvPV RDgTSTNRTL DGDPrTFPLG rPLYADFSHD
```

Figure 1/10

| | | |
|---|---|---|
| Consensus ATLYADFSHD | PAQGVGF-NE LIARLTHSPV | QDHTSTNHTL DSNPATFPLN |
| Consensus phytase ATLYADFSHD | PAQGVGFANE LIARLTRSPV | QDHTSTNHTL DSNPATFPLN |

```
                                          351                              400
A. terreus 9A-1         SNLVSIFWAL GLYNGTAPLS qTSVESVSQT DGYAAAWTVP FAARAYVEMM
A. terreus cbs          SNLVSIFWAL GLYNGTkPLS qTTVEDITrT DGYAAAWTVP FAARAYIEMM
A. niger var. awamori   NGIISILFAL GLYNGTkPLS TTTVENITQT DGFSSAWTVP FASRlYVEMM
A. niger T213           NGIISILFAL GLYNGTkPLS TTTVENITQT DGFSSAWTVP FASRlYVEMM
A. niger NRRL3135       NGIISILFAL GLYNGTkPLS TTTVENITQT DGFSSAWTVP FASRlYVEMM
A. fumigatus 13073      NSMVSIFFAL GLYNGTEPLS rTSVESaKEl DGYSASWVVP FGARAYFEtM
A. fumigatus 32722      NSMVSIFFAL GLYNGTGPLS rTSVESaKEl DGYSASWVVP FGARAYFEtM
A. fumigatus 58128      NSMVSIFFAL GLYNGTEPLS rTSVESaKEl DGYSASWVVP FGARAYFEtM
A. fumigatus 26906      NSMVSIFFAL GLYNGTEPLS rTSVESaKEl DGYSASWVVP FGARAYFEtM
A. fumigatus 32239      NGMIPIFFAM GLYNGTEPLS qTSeESTKES NGYSASWAVP FGARAYFEtM
```

Figure 1/11

| | |
|---|---|
| A. nidulans | NSMISIFFAM GLYNGTQPLS mDSVESIQEm DGYAASWTVP FGARAYFELM |
| T. thermophilus | NTMTSIFaAL GLYNGTAkLS TTEIKSIEET DGYSAAWTVP FGGRAYIEMM |
| M. thermophila | NDMMGVLgAL GaYDGVPPLD KTArrDpEEl GGYAASWAVP FAARiYVEKM |
| Consensus | NSMISIFFAL GLYNGTAPLS TTSVESIEET DGYAASWTVP FGARAYVEMM |
| Consensus phytase | NSMISIFFAL GLYNGTAPLS TTSVESIEET DGYSASWTVP FGARAYVEMM |

```
                          401                                        450
A. terreus 9A-1        QC........ .....RAEKE PLVRVLVNDR VMPLHGCPTD KLGRCKrDAF
A. terreus cbs         QC........ .....RAEKQ PLVRVLVNDR VMPLHGCAVD NLGRCKrDDF
A. niger var. awamori  QC........ .....QAEQE PLVRVLVNDR VVPLHGCPID aLGRCTrDSF
A. niger T213          QC........ .....QAEQE PLVRVLVNDR VVPLHGCPID aLGRCTrDSF
A. niger NRRL3135      QC........ .....QAEQE PLVRVLVNDR VVPLHGCPVD aLGRCTrDSF
A. fumigatus 13073     QC........ .....KSEKE PLVRALINDR VVPLHGCDVD KLGRCKLNDF
A. fumigatus 32722     QC........ .....KSEKE PLVRALINDR VVPLHGCDVD KLGRCKLNDF
```

Figure 1/12

```
A. fumigatus 58128    QC........ .....KSEKE SLVRALINDR VVPLHGCDVD
KLGRCKLNDF
A. fumigatus 26906    QC........ .....KSEKE PLVRALINDR VVPLHGCDVD
KLGRCKLNDF
A. fumigatus 32239    QC........ .....KSEKE PLVRALINDR VVPLHGCAVD
KLGRCKLKDF
A. nidulans           QC........ .....E.KKE PLVRVLVNDR VVPLHGCAVD
KFGRCTLDDW
T. thermophilus       QC........ .....DDSDE PVVRVLVNDR VVPLHGCEVD
SLGRCKrDDF
M. thermophila        RCsggggggg ggegrQEKDE eMVRVLVNDR VMTLkGCGAD
ErGMCTLErF Consensus             QC-------- -----QAEKE PLVRVLVNDR VVPLHGCAVD
KLGRCKLDDF
Consensus phytase     QC........ .....QAEKE PLVRVLVNDR VVPLHGCAVD
KLGRCKRDDF
```

Figure 1/13

```
                              451              471
A. terreus 9A-1          VAGLSFAQAG  GNWADCF~~~  ~
A. terreus cbs           VEGLSFARAG  GNWAECF~~~  ~
A. niger var. awamori    VrGLSFARSG  GDWAECsA~~  ~
A. niger T213            VrGLSFARSG  GDWAECFA~~  ~
A. niger NRRL3135        VrGLSFARSG  GDWAECFA~~  ~
A. fumigatus 13073       VKGLSWARSG  GNWGECFS~~  ~
A. fumigatus 32722       VKGLSWARSG  GNWGECFS~~  ~
A. fumigatus 58128       VKGLSWARSG  GNWGECFS~~  ~
A. fumigatus 26906       VKGLSWARSG  GNWGECFS~~  ~
A. fumigatus 32239       VKGLSWARSG  GNSEQSFS~~  ~
A. nidulans              VEGLNFARSG  GNWkTCFT1~  ~
T. thermophilus          VrGLSFARqG  GNWEGCYAas  e
M. thermophila           IESMAFARGN  GKWDlCFA~~  ~

Consensus                VEGLSFARSG  GNWAECFA--  -
Consensus phytase        VEGLSFARSG  GNWAECFA..  .
```

Figure 2/1

```
CP-1
     EcoRI  M  G  V  F  V  V  L  L  S  I  A  T  L  F  G  S  T
   TATATGAATTCATGGGCGTGTTCGTCGTGCTACTGTCCATTGCCACCTTGTTCGGTTCCA
 1 ---------+---------+---------+---------+---------+---------+ 60

ATATACTTAAGTACCCGCACAAGCAGCACGATGACAGGTAACGGTGGAACAAGCCAAGGT

S  G  T  A  L  G  P  R  G  N  S  H  C  D  T  V  D  G  G
   CATCCGGTACCGCCTTGGGTCCTCGTGGTAATTCTCACTCTTGTGACACTGTTGACGGTG
61 ---------+---------+---------+---------+---------+---------+ 120

GTAGGCCATGGCGGAACCCAGGAGCACCATTAAGAGTGAGAACACTGTGACAACTGCCAC
              CP-2
            CP-3
      Y  Q  C  F  P  E  I  S  H  L  W  G  Q  Y  S  P  Y  F  S  L
   GTTACCAATGTTTCCCAGAAATTTCTCACTTGTGGGGTCAATACTCTCCATACTTCTCTT
121 ---------+---------+---------+---------+---------+---------+ 180

CAATGGTTACAAAGGGTCTTTAAAGAGTGAACACCCCAGTTATGAGAGGTATGAAGAGAA

E  D  E  S  A  I  S  P  D  V  P  D  D  C  R  V  T  F  V  Q
   TGGAAGACGAATCTGCTATTTCTCCAGACGTTCCAGACGACTGTAGAGTTACTTTCGTTC
181 ---------+---------+---------+---------+---------+---------+ 240

ACCTTCTGCTTAGACGATAAAGAGGTCTGCAAGGTCTGCTGACATCTCAATGAAAGCAAG
                    CP-4
                  CP-5
      V  L  S  R  H  G  A  R  Y  P  T  S  S  K  S  K  A  Y  S  A
   AAGTTTTGTCTAGACACGGTGCTAGATACCCAACTTCTTCTAAGTCTAAGGCTTACTCTG
```

Figure 2/2

```
241 ----------+---------+---------+---------+---------+---------+
                                                                 300
    TTCAAAACAGATCTGTGCCACGATCTATGGGTTGAAGAAGATTCAGATTCCGAATGAGAC

L   I   E   A   I   Q   K   N   A   T   A   F   K   G   K   Y   A   F   L   K
    CTTTGATTGAAGCTATTCAAAAGAACGCTACTGCTTTCAAGGGTAAGTACGCTTTCTTGA
301 ----------+---------+---------+---------+---------+---------+
                                                                 360
    GAAACTAACTTCGATAAGTTTTCTTGCGATGACGAAAGTTCCCATTCATGCGAAAGAACT
                                      CP-6
                                          CP-7
      T   Y   N   Y   T   L   G   A   D   D   L   T   P   F   G   E   N   Q   M   V
    AGACTTACAACTACACTTTGGGTGCTGACGACTTGACTCCATTCGGTGAAAACCAAATGG
361 ----------+---------+---------+---------+---------+---------+
                                                                 420
    TCTGAATGTTGATGTGAAACCCACGACTGCTGAACTGAGGTAAGCCACTTTTGGTTTACC

N   S   G   I   K   F   Y   R   R   Y   K   A   L   A   R   K   I   V   P   F
    TTAACTCTGGTATTAAGTTCTACAGAAGATACAAGGCTTTGGCTAGAAAGATTGTTCCAT
421 ----------+---------+---------+---------+---------+---------+
                                                                 480
    AATTGAGACCATAATTCAAGATGTCTTCTATGTTCCGAAACCGATCTTTCTAACAAGGTA
                                               CP-8
                                                   CP-9
```

Figure 2/3

```
            I   R   A   S   G   S   D   R   V   I   A   S   A   E   K   F   I   E   G   F
        TCATTAGAGCTTCTGGTTCTGACAGAGTTATTGCTTCTGCTGAAAAGTTCATTGAAGGTT
    481 ---------+---------+---------+---------+---------+---------+
540
        AGTAATCTCGAAGACCAAGACTGTCTCAATAACGAAGACGACTTTTCAAGTAACTTCCAA

Q   S   A   K   L   A   D   P   G   S   Q   P   H   Q   A   S   P   V   I   D
        TCCAATCTGCTAAGTTGGCTGACCCAGGTTCTCAACCACACCAAGCTTCTCCAGTTATTG
    541 ---------+---------+---------+---------+---------+---------+
600
        AGGTTAGACGATTCAACCGACTGGGTCCAAGAGTTGGTGTGGTTCGAAGAGGTCAATAAC
                                                             CP-10

CP-11
            V   I   I   P   E   G   S   G   Y   N   N   T   L   D   H   G   T   C   T   A
        ACGTTATTATTCCAGAAGGaTCcGGTTACAACAACACTTTGGACCACGGTACTTGTACTG
    601 ---------+---------+---------+---------+---------+---------+
660
        TGCAATAATAAGGTCTTCCtAGgCCAATGTTGTTGTGAAACCTGGTGCCATGAACATGAC
```

Figure 2/4

```
         F  E  D  S  E  L  G  D  D  V  E  A  N  F  T  A  L  F  A  P
      CTTTCGAAGACTCTGAATTGGGTGACGACGTTGAAGCTAACTTCACTGCTTTGTTCGCTC
  661 ---------+---------+---------+---------+---------+---------+
  720
      GAAAGCTTCTGAGACTTAACCCACTGCTGCAACTTCGATTGAAGTGACGAAACAAGCGAG
                                                                CP-12

A  I  R  A  R  L  E  A  D  L  P  G  V  T  L  T  D  E  D  V
      CAGCTATTAGAGCTAGATTGGAAGCTGACTTGCCAGGTGTTACTTTGACTGACGAAGACG
  721 ---------+---------+---------+---------+---------+---------+
  780
      GTCGATAATCTCGATCTAACCTTCGACTGAACGGTCCACAATGAAACTGACTGCTTCTGC

CP-13
         V  Y  L  M  D  M  C  P  F  E  T  V  A  R  T  S  D  A  T  E
      TTGTTTACTTGATGGACATGTGTCCATTCGAAACTGTTGCTAGAACTTCTGACGCTACTG
  781 ---------+---------+---------+---------+---------+---------+
  840
      AACAAATGAACTACCTGTACACAGGTAAGCTTTGACAACGATCTTGAAGACTGCGATGAC

L  S  P  F  C  A  L  F  T  H  D  E  W  R  Q  Y  D  Y  L  Q
      AATTGTCTCCATTCTGTGCTTTGTTCACTCACGACGAATGGAGACAATACGACTACTTGC
  841 ---------+---------+---------+---------+---------+---------+
  900
      TTAACAGAGGTAAGACACGAAACAAGTGAGTGCTGCTTACCTCTGTTATGCTGATGAACC
            CP-14
                CP-15
         S  L  G  K  Y  Y  G  Y  G  A  G  N  P  L  G  P  A  Q  G  V
```

Figure 2/5

```
         AATCTTTGGGTAAGTACTACGGTTACGGTGCTGGTAACCCATTGGGTCCAGCTCAAGGTG
    901 ----------+---------+---------+---------+---------+---------+
960
         TTAGAAACCCATTCATGATGCCAATGCCACGACCATTGGGTAACCCAGGTCGAGTTCCAC

G   F   A   N   E   L   I   A   R   L   T   R   S   P   V   Q   D   H   T   S
         TTGGTTTCGCTAACGAATTGATTGCTAGATTGACTAGATCTCCAGTTCAAGACCACACTT
    961 ----------+---------+---------+---------+---------+---------+
1020
         AACCAAAGCGATTGCTTAACTAACGATCTAACTGATCTAGAGGTCAAGTTCTGGTGTGAA
                              CP-16
                                 CP-17
           T   N   H   T   L   D   S   N   P   A   T   F   P   L   N   A   T   L   Y   A
         CTACTAACCACACTTTGGACTCTAACCCAGCTACTTTCCCATTGAACGCTACTTTGTACG
   1021 ----------+---------+---------+---------+---------+---------+
1080
         GATGATTGGTGTGAAACCTGAGATTGGGTCGATGAAAGGGTAACTTGCGATGAAACATGC

D   F   S   H   D   N   S   M   I   S   I   F   F   A   L   G   L   Y   N   G
         CTGACTTCTCTCACGACAACTCTATGATTTCTATTTTCTTCGCTTTGGGTTTGTACAACG
   1081 ----------+---------+---------+---------+---------+---------+
1140
         GACTGAAGAGAGTGCTGTTGAGATACTAAAGATAAAAGAAGCGAAACCCAAACATGTTGC
                                  CP-18
                                     CP-19
           T   A   P   L   S   T   T   S   V   E   S   I   E   E   T   D   G   Y   S   A
         GTACTGCTCCATTGTCTACTACTTCTGTTGAATCTATTGAAGAAACTGACGGTTACTCTG
```

Figure 2/6

```
1141 ---------+---------+---------+---------+---------+---------+
1200
        CATGACGAGGTAACAGATGATGAAGACAACTTAGATAACTTCTTTGACTGCCAATGAGAC

S   W   T   V   P   F   G   A   R   A   Y   V   E   M   M   Q   C   Q   A   E
        CTTCTTGGACTGTTCCATTCGGTGCTAGAGCTTACGTTGAAATGATGCAATGTCAAGCTG
1201 ---------+---------+---------+---------+---------+---------+
1260
        GAAGAACCTGACAAGGTAAGCCACGATCTCGAATGCAACTTTACTACGTTACAGTTCGAC
                                              CP-20
                                                CP-21
         K   E   P   L   V   R   V   L   V   N   D   R   V   V   P   L   H   G   C   A
        AAAAGGAACCATTGGTTAGAGTTTTGGTTAACGACAGAGTTGTTCCATTGCACGGTTGTG
1261 ---------+---------+---------+---------+---------+---------+
1320
        TTTTCCTTGGTAACCAATCTCAAAACCAATTGCTGTCTCAACAAGGTAACGTGCCAACAC
```

Figure 2/7

```
        V   D   K   L   G   R   C   K   R   D   D   F   V   E   G   L   S   F   A   R
     CTGTTGACAAGTTGGGTAGATGTAAGAGAGACGACTTCGTTGAAGGTTTGTCTTTCGCTA
1321 ---------+---------+---------+---------+---------+---------+
1380
     GACAACTGTTCAACCCATCTACATTCTCTCTGCTGAAGCAACTTCCAAACAGAAAGCGAT
                                                        CP-22

S   G   G   N   W   A   E   C   F   A   *   Eco RI
     GATCTGGTGGTAACTGGGCTGAATGTTTCGCTTAAGAATTCATATA
1381 ---------+---------+---------+---------+------ 1426
     CTAGACCACCATTGACCCGACTTACAAAGCGAATTCTTAAGTATAT
```

CONSENSUS PHYTASES

BACKGROUND OF THE INVENTION

Phytases (myo-inositol hexakisphosphate phosphohydrolases; EC 3.1.3.8) are enzymes that hydrolyze phytate (myo-inositol hexakisphosphate) to myo-inositol and inorganic phosphate and are known to be valuable feed additives.

A phytase was first described in rice bran in 1907 [Suzuki et al., Bull. Coll. Agr. Tokio Imp. Univ. 7, 495 (1907)] and phytases from Aspergillus species in 1911 [Dox and Golden, J. Biol. Chem. 10, 183–186 (1911)]. Phytases have also been found in wheat bran, plant seeds, animal intestines and in microorganisms [Howsen and Davis, Enzyme Microb. Technol. 5, 377–382 (1983), Lambrechts et al., Biotech. Lett. 14, 61–66 (1992), Shieh and Ware, Appl. Microbiol. 16, 1348–1351 (1968)].

The cloning and expression of the phytase from *Aspergillus niger* (*ficuum*) has been described by Van Hartingsveldt et al., in Gene, 127, 87–94 (1993) and in European Patent Application, Publication No. (EP) 420 358 and from *Aspergillus niger* var. *awamori* by Piddington et al., in Gene 133, 55–62 (1993).

Cloning, expression and purification of phytases with improved properties have been disclosed in EP 684 313. However, since there is a still ongoing need for further improved phytases, especially with respect to their thermostability, it is an object of the present invention to provide the following process which is, however, not only applicable to phytases.

SUMMARY OF THE INVENTION

The invention herein is a process for the preparation of a consensus protein, especially a phytase. The invention is also directed to a consensus phytase and to a DNA sequence encoding the consensus phytase. As is well known, a consensus protein is a new protein whose sequence is created from sequence information obtained from at least three other proteins having a similar biological activity. The object in preparing a consensus protein is to obtain a single protein which combines the advantageous properties of the original proteins.

The process is characterized by the following steps:

a) at least three preferably four amino acid sequences of a defined protein family are aligned by any standard alignment program known in the art;

b) amino acids at the same position according to such alignment are compared regarding their evolutionary similarity by any standard program known in the art, whereas the degree of similarity provided by such a program which defines the least similarity of the amino acids that is used for the determination of an amino acid of corresponding positions is set to a less stringent number and the parameters are set in such a way that it is possible for the program to determine from only 2 identical amino acids at a corresponding position an amino acid for the consensus protein; however, if among the compared amino acid sequences are sequences that show a much higher degree of similarity to each other than to the residual sequences, these sequences are represented by their consensus sequence determined as defined in the same way as in the present process for the consensus sequence of the consensus protein or a vote weight of 1 divided by the number of such sequences is assigned to every of those sequences.

c) in case no common amino acid at a defined position can be identified by the program, any of the amino acids of all sequences used for the comparison, preferably the most frequent amino acid of all such sequences is selected or an amino acid is selected on the basis of the consideration given in Example 2.

d) once the consensus sequence has been defined, such sequence is back-translated into a DNA sequence, preferably using a codon frequency table of the organism in which expression should take place;

e) the DNA sequence is synthesized by methods known in the art and used either integrated into a suitable expression vector or by itself to transform an appropriate host cell;

f) the transformed host cell is grown under suitable culture conditions and the consensus protein is isolated from the host cell or its culture medium by methods known in the art.

In a preferred embodiment of this process step b) can also be defined as follows: b) amino acids at the same position according to such an alignment are compared regarding their evolutionary similarity by any standard program known in the art, whereas the degree of similarity provided by such program is set at the lowest possible value and the amino acid which is the most similar for at least half of the sequences used for the comparison is selected for the corresponding position in the amino acid sequence of the consensus protein.

Thus the claimed invention is a process for obtaining a consensus protein from a group of amino acid sequences of a defined protein family, which comprises:

a) aligning a group consisting of three to one hundred, but preferably three or four amino acid sequences from a defined protein family;

b) comparing the evolutionary similarity of amino acids which occupy a position in the aligned sequences to select a consensus amino acid for said position using a system which is so organized that if two amino acids which occupy said position are identical, then the identical amino acid is selected as the consensus amino acid for said position, unless three or more other amino acids at said position have a higher degree of structural similarity to each other than to the identical amino acid, in which case the amino acid which has the highest degree of evolutionary similarity to the other amino acids is selected as the consensus amino acid for said position, with the proviso that if a set of amino acid sequences exists within the group of step a) such that the amino acid sequences within the set have more evolutionary similarity to each other than to any of the amino acid sequences of the group which are not part of the set, then the amino acids which occupy said position in members of the set will have a vote weight of one divided by the number of amino acid sequences in the set where the amino acids which occupy said position in amino acid sequences which are not in the set will have a vote weight of one, and repeating the procedure for each position in the aligned group of amino acid sequences;

c) if no consensus amino acid for said position is obtained by the method of step b), then any amino acid at said position is selected as the consensus sequence, preferably the most frequent amino acid;

d) combining the consensus amino acids obtained in steps b) and c) to obtain a consensus amino acid sequence;

e) translating the consensus amino acid sequence into a DNA sequence, preferably using a codon frequency table specific to whichever host organism has been selected for expressing the DNA sequence;

f) obtaining the DNA sequence and using said DNA sequence to express a protein which is the consensus protein of the defined protein family.

The present invention is also directed to new phytases, preferably phytases having the amino acid sequence depicted in FIG. 2 and variants and muteins thereof. In addition, the invention includes polynucleotides which encode such new phytases.

A BRIEF DESCRIPTION OF THE DRAWINGS

FIG. 1: Calculation of the consensus phytase sequence from the alignment of nearly all known fungal phytase amino acid sequences. The letters represent the amino acid residues in the one-letter code. The following sequences were used for the alignment: phyA from *Aspergillus terreus* 9A-1 (Mitchell et al., 1997; from amino acid (aa) 27), phyA from *Aspergillus terreus* cbs116.46 (van Loon et al., 1997; from aa 27), phyA from *Aspergillus niger* var. *awamori* (Piddington et al., 1993; from aa 27), phyA from *Aspergillus niger* T213; from aa 27), phyA from *Aspergillus niger* strain NRRL3135 (van Hartingsveldt et al., 1993; from aa 27), phyA from *Aspergillus fumigatus* ATCC 13073 (Pasamontes et al., 1997b; from aa 25), phyA from *Aspergillus fumigatus* ATCC 32722 (van Loon et al., 1997; from aa 27), phyA from *Aspergillus fumigatus* ATCC 58128 (van Loon et al., 1997; from aa 27), phyA from *Aspergillus fumigatus* ATCC 26906 (van Loon et al., 1997; from aa 27), phyA from *Aspergillus fumigatus* ATCC 32239 (van Loon et al., 1997; from aa 30), phyA from *Aspergillus nidulans* (Pasamontes et al., 1997a; from aa 25), phyA from *Talaromyces thermophilus* (Pasamontes et al., 1997a; from aa 24), and phyA from *Myceliophthora thermophila* Mitchell et al., 1997; from aa 19). The alignment was calculated using the program PILEUP. The location of the gaps was refined by hand. Capitalized amino acid residues in the alignment at a given position belong to the amino acid coalition that establish the consensus residue. In bold, beneath the calculated consensus sequence, the amino acid sequence of the finally constructed fungal consensus phytase (Fcp) (SEQ ID NO:1) is shown. The gaps in the calculated consensus sequence were filled by hand according to principals stated in Example 2.

FIG. 2: DNA sequence of the fungal consensus phytase gene (fcp) (SEQ ID:3) and of the primers synthesized for gene construction. The calculated amino acid sequence (FIG. 1) (SEQ ID:1) was converted into a DNA sequence using the program BACKTRANSLATE (Devereux et al., 1984) and the codon frequency table of highly expressed yeast genes (GCG program package, 9.0). The signal peptide of the phytase from *A. terreus* cbs was fused to the N-terminus. The bold bases represent the sequences of the oligonucleotides used to generate the gene. The names of the respective oligonucleotides are noted above or below the sequence. The underlined bases represent the start and stop codon of the gene. The bases written in italics show the two introduced Eco RI sites.

FIG. 3: Temperature optimum of fungal consensus phytase and other phytases used to calculate the consensus sequence. For the determination of the temperature optimum, the phytase standard assay was performed at a series of temperatures between 37 and 85° C. The phytases used were purified according to Example 5. ▽, fungal consensus phytase; ▼, *A. fumigatus* 13073 phytase; □, *A. niger* NRRL3135 phytase; ○, *A. nidulans* phytase; ■, *A. terreus* 9A-1 phytase; •, *A. terreus* cbs phytase.

FIG. 4: The pH-dependent activity profile of fungal consensus phytase and of the mutant Q50L, Q50T, and Q50G. The phytase activity was determined using the standard assay in appropriate buffers (see Example 9) at different pH-values. Plot a) shows a comparison of fungal consensus phytase (•) to the mutants Q50L (▽), Q50T (▼), and Q50G (○) in percent activity. Plot b) shows a comparison of fungal consensus phytase (○) to mutant Q50L (•) and Q50T (▽) using the specific activity of the purified enzymes expressed in *H. polymorpha*.

FIG. 5: The pH-dependent activity profile of the mutants Q50L, Y51N and Q50T, Y51N in comparison to the mutants Q50T and Q50L of fungal consensus phytase. The phytase activity was determined using the standard assay in appropriate buffers (see Example 9) at different pH-values. Graph a) shows the influence of the mutation Y51N (•) on mutant Q50L (○). Graph b) shows the influence of the same mutation (•) on mutant Q50T (○).

FIG. 6: Substrate specificity of fungal consensus phytase and its mutants Q50L, Q50T, and Q50G. The bars represent the relative activity in comparison to the activity with phytic acid (100%) with a variety of known natural and synthetic phosphorylated compounds.

FIG. 7: Differential scanning calorimetry (DSC) of fungal consensus phytase and its mutant Q50T. The protein samples were concentrated to ca. 50–60 mg/ml and extensively dialyzed against 10 mM sodium acetate, pH 5.0. A constant heating rate of 10° C./min was applied up to 90° C. DSC of consensus phytase Q50T (upper graph) yielded in a melting temperature of 78.9° C., which is nearly identical to the melting point of fungal consensus phytase (78.1° C., lower graph).

DETAILED DESCRIPTION OF THE INVENTION

Figure 3:
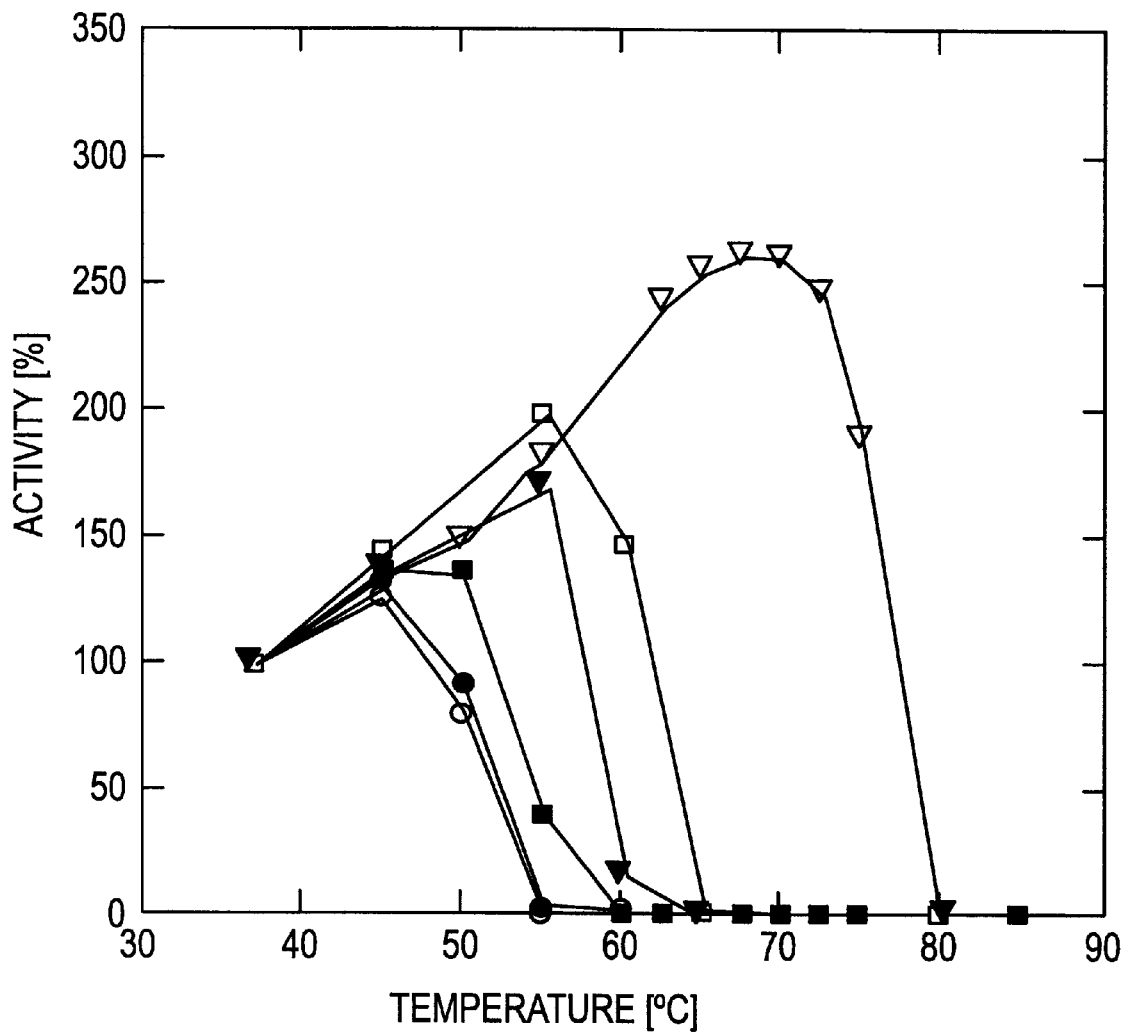

A preferred embodiment of this whole process can be seen in a process in which a sequence is choosen from a number of highly homologous sequences and only those amino acid residues are replaced which clearly differ from a consensus sequence of this protein family calculated under moderately stringent conditions, while at all positions of the alignment where the method is not able to determine an amino acid under moderately stringent conditions the amino acids of the preferred sequence are taken.

It is furthermore an object of the present invention to provide such a process, wherein the program used for the comparison of amino acids at a defined position regarding their evolutionary similarity is the program "PRETTY". It is more specifically an object of the present invention to provide such a process, wherein the defined protein family is the family of phytases, especially wherein the phytases are of fungal origin.

It is furthermore an object of the present invention to provide such processes, wherein the host cell is of eukaryotic, especially fungal, preferably Aspergillus or yeast, preferably Saccharomyces or Hansenula origin. It is also an object of the present invention to provide a consensus protein obtainable by such a process. A preferred consensus protein obtained by the present process is of the defined protein family of phytases. The especially preferred consensus phytase is created based on phytase sequences from:

*Aspergillus terreus* 9A-1, aa 27 (Mitchell et al., 1997);
*Aspergillus terreus* cbs116.46, aa 27 (van Loon et al., 1997);
*Aspergillus niger* var. *awamori*, aa 27 (Piddington et al., 1993);
*Aspergillus niger* T213, aa 27;
*Aspergillus niger* strain NRRL3135, aa 27 (van Hartingsveldt et al., 1993);
*Aspergillus fumigatus* ATCC 13073, aa 26 (Pasamontes et al., 1997);

*Aspergillus fumigatus* ATCC 32722, aa 26 (van Loon et al., 1997);
*Aspergillus fumigatus* ATCC 58128, aa 26 (van Loon et al., 1997);
*Aspergillus fumigatus* ATCC 26906, aa 26 (van Loon et al., 1997);
*Aspergillus fumigatus* ATCC 32239, aa 30 (van Loon et al., 1997);
*Aspergillus nidulans*, aa 25 (Pasamontes et al., 1997a);
*Talaromyces thermophilus* ATCC 20186, aa 24 (Pasamontes et al., 1997a); and
*Myceliophthora thermophila*, aa 19 (Mitchell et al., 1997).

Therefore the preferred group of amino acid sequences used in the process of this invention is the amino acid sequences encoding the phytases of the above fungi.

The preferred phytase of the invention is a consensus protein whose sequence is created based on the sequences of the twelve phytases shown in Table 3, below, but which is not highly homologous to any of the twelve phytases in that the consensus phytase is not more than about 80% identical to any of the twelve phytases. The present invention is particularly directed to a consensus phytase which has the amino acid sequence shown in FIG. 2 (SEQ ID:2) or a variant or mutein thereof. The consensus phytase of FIG. 2 (SEQ ID:2) is not highly homologous to any of the twelve phytases which were used to create its sequence, as can be seen from the sequence comparison results shown in Table 3. Another consensus phytase of this invention has the sequence shown in FIG. 1 as consensus phytase (bottom line in boldface type) or a variant or mutein thereof.

A "variant" of the consensus phytase with amino acid sequence shown in FIG. 1 or preferably FIG. 2 is the consensus phytase of FIG. 1 or preferably FIG. 2 in which at one or more positions amino acids have been deleted, added or replaced by one or more other amino acids with the proviso that the resulting sequence provides for a phytase whose basic properties like enzymatic activity (type of and specific activity), thermostability, activity in a certain pH-range (pH-stability) have not significantly been changed. "Significantly" means in this context that a skilled person would say that the properties of the variant may still be different but would not be unobvious over the ones of the consensus phytase with the amino acid sequence of FIG. 1 (SEQ ID:1) or FIG. 2 (SEQ ID:2) itself.

A mutein refers in the context of the present invention to replacements of the amino acid in the amino acid sequence of the consensus protein shown in FIG. 1 (SEQ ID:1) o preferably FIG. 2 (SEQ ID:2) which lead to consensus proteins with further improved properties, e. g., activity. Such muteins can be defined and prepared on the basis of the teachings given in European Patent Application number 97810175.6, e. g., Q50L, Q50T, Q50G, Q50L-Y51N, or Q50T-Y51N. "Q50L" means in this context that at position 50 of the amino acid sequence the amino acid Q has been replaced by amino acid L. Therefore specific muteins of this invention include a mutein which has the amino acid sequence of FIG. 2 (SEQ ID:2) except that Q at position 50 has been replaced by L, T, or G, and two muteins which have the amino acid sequence of FIG. 1 (SEQ ID:1) except that Q at position 50 has been replaced by T or L and Y at position 51 has been replaced by N.

Polynucleotides which encode the consensus phytase of this invention, i.e., a phytase with the amino acid sequence of FIG. 1 (SEQ ID:1) or preferably FIG. 2 (SEQ ID:2) or variants and muteins thereof, especially the specific muteins listed above, are also part of this invention. Such polynucleotides may be obtained by known methods, for example by backtranslation of the mutein's amino acid sequence and PCR synthesis of the corresponding polynucleotide as described below.

In addition, a food, feed, premix or pharmaceutical composition comprising a consensus protein as defined above is also an object of the present invention. Food, feed, and premix compositions, preferably for domestic livestock, are well known to a skilled person, as are pharmaceutical compositions. Such pharmaceutical compositions are likely to be veterinary compositions formulated for oral ingestion, such as pills and the like.

In this context "at least three preferably four amino acid sequences of such defined protein family" means that three, four, five, six to 12, 20, 50, 100 or even more sequences can be used for the alignment and the comparison to create the amino acid sequence of the consensus protein. Amino acid sequences may be obtained from known sources such as publications or databases, or may be deduced by translation of DNA sequences which are publicly available, or may be determined by known techniques for sequencing an isolated protein or obtaining and sequencing a gene encoding a protein and translating the DNA sequence. "Sequences of a defined protein family" means that such sequences fold into a three dimensional structure, wherein the α-helixes, the β-sheets and-turns are at the same position so that such structures are, as called by the skilled person, superimposable. Furthermore these sequences characterize proteins which show the same type of biological activity, e.g., a defined enzyme class such as the phytases. As known in the art, the three dimensional structure of one of such sequences is sufficient to allow the modelling of the structure of the other sequences of such a family. An example, how this can be effected, is given in the Reference Example of the present case.

Aligning amino acid sequences is a well known process whereby two or more amino acids are lined up in such a way to maximize the internal amino acid sequences which they have in common.

"Evolutionary similarity" in the context of the present invention refers to a schema which classifies amino acids regarding their structural similarity which allows that one amino acid can be replaced by another amino acid with a minimal influence on the overall structure, as this is done e.g. by programs, like "PRETTY", known in the art. The phrase "the degree of similarity provided by such a program . . . is set to less stringent number" means in the context of the present invention that values for the parameters which determine the degree of similarity in the program used in the practice of the present invention are chosen in a way to allow the program to define a common amino acid for a maximum of positions of the whole amino acid sequence, e. g. in case of the program PRETTY a value of 2 or 3 for the THRESHOLD and a value of 2 for the PLURALITY can be choosen.

A consensus amino acid is an amino acid chosen to occupy a given position in the consensus protein obtained by this method. A system which is organized to select consensus amino acids as described above may be a computer program, or a combination of one or more computer programs with "by hand" analysis and calculation. A set of amino acid sequences existing within the group of amino acid sequences from which the consensus sequence is prepared means a set of such sequences which are more similar to each other than to other members of the group, based on the evolutionary similarity analysis performed above. An example of such a group is a species where a set with in the group would be members of a particular strain. Furthermore, "a vote weight of one divided by the number of such sequences" means in the context of the present invention that the sequences which define a group of sequences with a higher degree of similarity as the other sequences used for the determination of the consensus sequence only contribute to such determination with a factor which is equal to one divided by a number of all sequences of this group. Thus an amino acid occupying a particular position in the aligned sequences will, if it is a member of a set, not have a comparison value of equal weight with the other amino acids (e.g. one) but will have a lower weight depending on the size of the set which it is in, as the weight is one divided by the number of amino acid sequences in the set.

When a consensus amino acid is obtained for each position of the aligned amino acid sequences, then these consensus amino acids are "lined up" to obtain the amino acid sequence of the consensus protein.

As mentioned before should the program not allow selection of the most similar amino acid, the most frequent amino acid is selected, should the latter be impossible the skilled person will select an amino acid from all the sequences used for the comparison which is known in the art for its property to improve the thermostability in proteins as discussed, e.g., by:

Janecek, S. (1993), *Process Biochem.* 28, 435–445 or
Fersht, A. R. & Serrano, L. (1993), *Curr. Opin. Struct. Biol.* 3, 75–83.
Alber, T. (1989), *Annu. Rev. Biochem.* 58, 765–798 or
Matthews, B. W. (1987), *Biochemistry* 26, 6885–6888.
Matthews, B. W. (1991), *Curr. Opin. Struct. Biol.* 1, 17–21.

The stability of an enzyme is a critical factor for many industrial applications. Therefore, a lot of attempts, more or less successful, have been made to improve the stability, preferably the thermostability, of enzymes by rational (van den Burg et al., 1998) or irrational approaches (Akanuma et al., 1998). The forces influencing the thermostability of a protein are the same as those that are responsible for the proper folding of a peptide strand (hydrophobic interactions, van der Waals interactions, H-bonds, salt bridges, conformational strain (Matthews, 1993). Furthermore, as shown by Matthews et al. (1987), the free energy of the unfolded state has also an influence on the stability of a protein. Enhancing of protein stability means to increase the number and strength of favorable interactions and to decrease the number and strength of unfavorable interactions. It has been possible to introduce disulfide linkages (Sauer et al., 1986) to replace glycine with alanine residues or to increase the proline content in order to reduce the free energy of the unfolded state (Margarit et al., 1992; Matthews, 1987a). Other groups concentrated on the importance of additional H-bonds or salt bridges for the stability of a protein (Blaber et al., 1993) or tried to fill cavities in the protein interior to increase the buried hydrophobic surface area and the van der Waals interactions (Karpusas et al., 1989). Furthermore, the stabilization of secondary structure elements, especially α-helices, for example, by improved helix capping, was also investigated (Munoz & Serrano, 1995).

However, there is no fast and promising strategy to identify amino acid replacements which will increase the stability, preferably the thermal stability of a protein. Commonly, the 3D structure of a protein is required to find locations in the molecule where an amino acid replacement possibly will stabilize the protein's folded state. Alternative ways to circumvent this problem are either to search for a homologous protein in a thermo- or hyperthermophile organism or to detect stability-increasing amino acid replacements by a random mutagenesis approach. This latter possibility succeeds in only $10^3$ to $10^4$ mutations and is restricted to enzymes for which a fast screening procedure is available (Arase et al., 1993; Risse et al., 1992). For all these approaches, success was variable and unpredictable and, if successful, the thermostability enhancements nearly always were rather small.

Here we present an alternative way to improve the thermostability of a protein. Imanaka et al. (1986) were among the first to use the comparisons of homologous proteins to enhance the stability of a protein. They used a comparison of proteases from thermophilic with homologous ones of mesophilic organisms to enhance the stability of a mesophilic protease. Serrano et al. (1993) used the comparison of the amino acid sequences of two homologous mesophilic RNases to construct a more thermostable Rnase. They mutated individually all of the residues that differ between the two and combined the mutations that increase the stability in a multiple mutant. Pantoliano et al. (1989) and, in particular, Steipe et al. (1994) suggested that the most frequent amino acid at every position of an alignment of homologous proteins contribute to the largest amount to the stability of a protein. Steipe et al. (1994) proved this for a variable domain of an immunoglobulin, whereas Pantoliano et al. (1989) looked for positions in the primary sequence of subtilisin in which the sequence of the enzyme chosen to be improved for higher stability was singularly divergent. Their approach resulted in the replacement M50F which increased the $T_m$ of subtilisin by 1.8° C.

Steipe et al. (1994) proved on a variable domain of immunoglobulin that it is possible to predict a stabilizing mutation with better than 60% success rate just by using a statistical method which determines the most frequent amino acid residue at a certain position of this domain. It was also suggested that this method would provide useful results not only for stabilization of variable domains of antibodies but also for domains of other proteins. However, it was never mentioned that this method could be extended to the entire protein. Furthermore, nothing is said about the program which was used to calculate the frequency of amino acid residues at a distinct position or whether scoring matrices were used as in the present case.

It is therefore an object of the present invention to provide a process for the preparation of a consensus protein comprising a process to calculate an amino acid residue for nearly all positions of a so-called consensus protein and to synthesize a complete gene from this sequence that could be expressed in a pro- or eukaryotic expression system.

DNA sequences from which amino acid sequences may be derived for making consensus proteins of the present invention, can be constructed starting from genomic or cDNA sequences coding for proteins, e.g. phytases known in the state of the art [for sequence information see references mentioned above, e.g. EP 684 313 or sequence data bases, for example like Genbank (Intelligenetics, California, USA), European Bioinformatics Institute (Hinston Hall, Cambridge, GB), NBRF (Georgetown University, Medical Centre, Washington DC, USA) and Vecbase (University of Wisconsin, Biotechnology Centre, Madison, Wis., USA) or disclosed in the figures by methods of in vitro mutagenesis [see e.g. Sambrook et al., Molecular Cloning, Cold Spring Harbor Laboratory Press, New York]. A widely used strategy for such "site directed mutagenesis", as originally outlined by Hurchinson and Edgell [J. Virol. 8, 181 (1971)], involves the annealing of a synthetic oligonucleotide carrying the desired nucleotide substitution to a target region of a single-stranded DNA sequence wherein the mutation should be introduced [for review see Smith, Annu. Rev. Genet. 19, 423 (1985) and for improved methods see references 2–6 in Stanssen et al., Nucl. Acid Res., 17, 4441–4454 (1989)].

Another possibility of mutating a given DNA sequence which is also preferred for the practice of the present invention is the mutagenesis by using the polymerase chain reaction (PCR). DNA as starting material can be isolated by methods known in the art and described e.g. in Sambrook et al. Molecular Cloning) from the respective strains. For strain information see, e.g., EP 684 313 or any depository authority indicated below. *Aspergillus niger* [ATCC 9142], *Myceliophthora thermophila* [ATCC 48102], *Talaromyces thermophilus* [ATCC 20186] and *Aspergillus fumigatus* [ATCC 34625] have been redeposited according to the conditions of the Budapest Treaty at the American Type Culture Cell Collection under the following accession numbers: ATCC 74337, ATCC 74340, ATCC 74338 and ATCC 74339, respectively. Amino acid sequences may be obtained by know methods from these DNA sequences for use in the process of this invention to obtain a consensus protein. It is however, understood that DNA encoding a consensus protein in accordance with the present invention can also be prepared in a synthetic manner as described, e.g. in EP 747 483 or the examples by methods known in the art.

Once complete DNA sequences of the present invention have been obtained (for example by synthesis based on backtranslation of a consensus protein obtained in accordance with the invention) they can be integrated into vectors by methods known in the art and described e.g. in Sambrook et al. (s.a.) to overexpress the encoded polypeptide in appropriate host systems. However, a skilled person knows that also the DNA sequences themselves can be used to transform the suitable host systems of the invention to get overexpression of the encoded polypeptide. Appropriate host systems are for example fungi, like Aspergilli, e.g. *Aspergillus niger* [ATCC 9142] or *Aspergillus ficuum* [NRRL 3135] or like Trichoderma, e.g. *Trichoderma reesei* or yeasts, like Saccharomyces, e.g. *Saccharomyces cerevisiae* or Pichia, like *Pichia pastoris*, or *Hansenula polymorpha*, e.g. *H. polymorpha* (DSM5215) or plants, as described, e.g. by Pen et al., Bio/Technology 11, 811–814 (1994). A skilled person knows that such microorganisms are available from depository authorities, e.g. the American Type Culture Collection (ATCC), the Centraalbureau voor Schimmelcultures (CBS) or the Deutsche Sammlung für Mikroorganismen und Zellkulturen GmbH (DSM) or any other depository authority as listed in the Journal "Industrial Property" [(1991) 1, pages 29–40]. Bacteria which can be used are e.g. *E. coli*, Bacilli as, e.g. *Bacillus subtilis* or Streptomyces, e.g. *Streptomyces lividans* (see e.g. Anné and Mallaert in FEMS Microbiol. Letters 114, 121 (1993). *E. coli*, which could be used are *E. coli* K12 strains e.g. M15 [described as DZ 291 by Villarejo et al. in J. Bacteriol. 120, 466–474 (1974)], HB 101 [ATCC No. 33694] or *E. coli* SG13009 [Gottesman et al., J. Bacteriol. 148, 265–273 (1981)].

Vectors which can be used for expression in fungi are known in the art and described e.g. in EP 420 358, or by Cullen et al. [Bio/Technology 5, 369–376 (1987)] or Ward in Molecular Industrial Mycology, Systems and Applications for Filamentous Fungi, Marcel Dekker, New York (1991), Upshall et al. [Bio/Technology 5, 1301–1304 (1987)] Gwynne et al. [Bio/Technology 5, 71–79 (1987)], Punt et al. [J. Biotechnol. 17, 19–34 (1991)] and for yeast by Sreekrishna et al. [J. Basic Microbiol. 28, 265–278 (1988), Biochemistry 28, 4117–4125 (1989)], Hitzemann et al. [Nature 293, 717–722 (1981)] or in EP 183 070, EP 183 071, EP 248 227, EP 263 311. Suitable vectors which can be used for expression in *E. coli* are mentioned, e.g. by Sambrook et al. [s.a.] or by Fiers et al. in Procd. 8th Int. Biotechnology Symposium" [Soc. Franc. de Microbiol., Paris (Durand et al., eds.), pp. 680–697 (1988)] or by Bujard et al. in Methods in Enzymology, eds. Wu and Grossmann, Academic Press, Inc. Vol. 155, 416–433 (1987) and Stüber et al. in Immunological Methods, eds. Lefkovits and Pernis, Academic Press, Inc., Vol. IV, 121–152 (1990). Vectors which could be used for expression in Bacilli are known in the art and described, e.g. in EP 405 370, Procd. Natl. Acad. Sci. USA 81, 439 (1984) by Yansura and Henner, Meth. Enzymol. 185, 199–228 (1990) or EP 207 459. Vectors which can be used for the expression in *H. polymorpha* are known in the art and described, e.g. in Gellissen et al., Biotechnology 9, 291–295 (1991).

Either such vectors already carry regulatory elements, e.g., promotors, or the DNA sequences of the present invention can be engineered to contain such elements. Suitable promotor elements which can be used are known in the art and are, e.g. for *Trichoderma reesei* the cbh1- [Haarki et al., Biotechnology 7, 596–600 (1989)] or the pki1-promotor [Schindler et al., Gene 130, 271–275 (1993)], for *Aspergillus oryzae* the amy-promotor [Christensen et al., Abstr. 19th Lunteren Lectures on Molecular Genetics F23 (1987), Christensen et al., Biotechnology 6, 1419–1422 (1988), Tada et al., Mol. Gen. Genet. 229, 301 (1991)], for *Aspergillus niger* the glaA- [Cullen et al., Bio/Technology 5, 369–376 (1987), Gwynne et al., Bio/Technology 5, 713–719 (1987), Ward in Molecular Industrial Mycology, Systems and Applications for Filamentous Fungi, Marcel Dekker, New York, 83–106 (1991)], alcA- [Gwynne et al., Bio/Technology 5, 718–719 (1987)], suc1- [Boddy et al., Curr. Genet. 24, 60–66 (1993)], aphA- [MacRae et al., Gene 71, 339–348 (1988), MacRae et al., Gene 132, 193–198 (1993)], tpiA- [McKnight et al., Cell 46, 143–147 (1986), Upshall et al., Bio/Technology 5, 1301–1304 (1987)], gpdA- [Punt et al., Gene 69, 49–57 (1988), Punt et al., J. Biotechnol. 17, 19–37 (1991)] and the pkiA-promotor [de Graaff et al., Curr. Genet. 22, 21–27 (1992)]. Suitable promotor elements which could be used for expression in yeast are known in the art and are, e.g. the pho5-promotor [Vogel et al., Mol. Cell. Biol., 2050–2057 (1989); Rudolf and Hinnen, Proc. Natl. Acad. Sci. 84, 1340–1344 (1987)] or the gap-promotor for expression in *Saccharomyces cerevisiae* and for *Pichia pastoris*, e.g. the aox1-promotor [Koutz et al., Yeast 5, 167–177 (1989); Sreekrishna et al., J. Basic Microbiol. 28, 265–278 (1988)], or the FMD promoter [Hollenberg et al., EPA No. 0299108] or MOX-promotor [Ledeboer et al., Nucleic Acids Res. 13, 3063–3082 (1985)] for *H. polymorpha*.

Accordingly vectors comprising DNA sequences of the present invention, preferably for the expression of said DNA sequences in bacteria or a host cells of eukaryotic origin, for example a fungal or a yeast host and such transformed bacteria or fungal or yeast hosts are also an object of the present invention.

It is also an object of the present invention to provide a system which allows for high expression of proteins, preferably phytases like the consensus phytase of the present invention in Hansenula or Saccharomyces characterized therein that the codons of the encoding DNA sequence of such a protein have been selected on the basis of a codon frequency table of the organism used for expression, e.g. yeast as in the present case (see e.g. in Example 3) and optionally the codons for the signal sequence have been selected in a manner as described for the specific case in Example 3. That means that a codon frequency table is prepared on the basis of the codons used in the DNA sequences which encode the amino acid sequences of the defined protein family. Then the codons for the design of the DNA sequence of the signal sequence are selected from a codon frequency table of the host cell used for expression whereby always codons of comparable frequency in both tables are used.

Once such DNA sequences have been expressed in an appropriate host cell in a suitable medium the encoded protein can be isolated either from the medium in the case the protein is secreted into the medium or from the host organism in case such protein is present intracellularly by methods known in the art of protein purification or described in case of a phytase, e.g. in EP 420 358. Accordingly a process for the preparation of a consensus protein (i.e. a polypeptide) of the present invention characterized in that transformed bacteria or a host cell as described above is cultured under suitable culture conditions and the consensus protein is recovered therefrom and a consensus protein produced by such a process or a consensus protein encoded by a DNA sequence of the present invention are also an object of the present invention.

Once obtained, the consensus proteins (i.e. polypeptides), preferably phytases, of the present invention can be characterized regarding their properties which make them useful in agriculture. Any assay known in the art may be used such as those described, e.g., by Simons et al. [Br. J. Nutr. 64, 525–540 (1990)], Schöner et al. [J. Anim. Physiol. a. Anim. Nutr. 66, 248–255 (1991)], Vogt [Arch. Geflügelk. 56, 93–98 (1992)], Jongbloed et al. [J. Anim. Sci., 70, 1159–1168 (1992)], Perney et al. [Poultry Sci. 72, 2106–2114 (1993)], Farrell et al., [J. Anim. Physiol. a. Anim. Nutr. 69, 278–283 (1993), Broz et al., [Br. Poultry Sci. 35, 273–280 (1994)] and Düngelhoef et al. [Animal Feed Sci. Technol. 49, 1–10 (1994)].

In general the consensus phytases of the present invention can be used without being limited to a specific field of application, e.g., in case of phytases for the conversion of inositol polyphosphates, like phytate to inositol and inorganic phosphate.

Furthermore the consensus phytases of the present invention can be used in a process for the preparation of a pharmaceutical composition or compound food or feeds wherein the components of such a composition are mixed with one or more consensus phytases of the present invention. Accordingly compound food or feeds or pharmaceutical compositions comprising one or more consensus phytases of the present invention, such as for example SEQ ID NO:2 or a variant or mutein thereof, are also an object of the present invention. A skilled person is familiar with their process of preparation. Such pharmaceutical compositions or compound foods or feeds can further comprise additives or components generally used for such purpose and known in the state of the art.

It is furthermore an object of the present invention to provide a process for the reduction of levels of phytate in animal manure characterized in that an animal is fed such a feed composition in an amount effective in converting phytate contained in the feedstuff to inositol and inorganic phosphate.

The Examples which follow further elucidate the invention but are not intended to limit it in any way.

EXAMPLES

Reference Example

Homology Modeling of *A. fumigatus* and *A. terreus* cbs116.46 Phytase

The amino acid sequences of *A. fumigatus* and *A. terreus* cbs116.46 phytase were compared with the sequence of *A. niger* NRRL 3135 phytase (see FIG. 1) for which the three-dimensional structure had been determined by X-ray crystallography.

A multiple amino acid sequence alignment of *A. niger* NRRL 3135 phytase, *A. fumigatus* phytase and *A. terreus* cbs116.46 phytase was calculated with the program "PILEUP" (Prog. Menu for the Wisconsin Package, version 8, September 1994, Genetics Computer Group, 575 Science Drive, Madison Wis., USA 53711). The three-dimensional models of *A. fumigatus* phytase and *A. terreus* cbs116.46 phytase were built by using the structure of *A. niger* NRRL 3135 phytase as template and exchanging the amino acids of *A. niger* NRRL 3135 phytase according to the sequence alignment to amino acids of *A. fumigatus* and *A. terreus* cbs116.46 phytases, respectively. Model construction and energy optimization were performed by using the program Moloc (Gerber and Müller, 1995). C-alpha positions were kept fixed except for new insertions/deletions and in loop regions distant from the active site.

Only small differences of the modelled structures to the original crystal structure could be observed in external loops. Furthermore the different substrate molecules that mainly occur on the degradation pathway of phytic acid (myo-inositol-hexakisphosphate) by Pseudomonas sp. *bacterium* phytase and, as far as determined, by *A. niger* NRRL 3135 phytase (Cosgrove, 1980) were constructed and forged into the active site cavity of each phytase structure. Each of these substrates was oriented in a hypothetical binding mode proposed for histidine acid phosphatases (Van Etten, 1982). The scissile phosphate group was oriented towards the catalytically essential His 59 to form the covalent phospho-enzyme intermediate. The oxygen of the substrate phospho-ester bond which will be protonated by Asp 339 after cleavage was orientated towards the proton donor. Conformational relaxation of the remaining structural part of the substrates as well as the surrounding active site residues was performed by energy optimization with the program Moloc.

Based on the structure models the residues pointing into the active site cavity were identified. More than half (60%) of these positions were identical between these three phytases, whereas only few positions were not conserved (see FIG. 1). This observation could be extended to four additional phytase sequences (*A. nidulans, A. terreus* 9A1, *Talaromyces thermophilus, Myceliophthora thermophila*).

EXAMPLE 1

Alignment of the Amino Acid Sequence of the Fungal Phytases

The alignment was calculated using the program PILEUP from the Sequence Analysis Package Release 9.0 (Devereux et al., 1984) with the standard parameter (gap creation penalty 12, gap extension penalty 4). The location of the gaps was refined using a text editor. Amino acid sequences encoded by the following genes (see FIG. 1) without the signal sequence were used for the performance of the alignment starting with the amino acid (aa) mentioned below:

phyA gene from *Aspergillus terreus* 9A-1, aa 27 (Mitchell et al., 1997)

phyA gene from *Aspergillus terreus* cbs116.46, aa 27 (van Loon et al., 1997)

phyA gene from *Aspergillus niger* var. *awamori*, aa 27 (Piddington et al., 1993)

phyA gene from *Aspergillus niger* T213, aa 27 phyA gene from *Aspergillus niger* strain NRRL3135, aa 27 (van Hartingsveldt et al., 1993)

phyA gene from *Aspergillus fumigatus* ATCC 13073, aa 26 (Pasamontes et al., 1997)

phyA gene from *Aspergillus fumigatus* ATCC 32722, aa 26 (van Loon et al., 1997)

phyA gene from *Aspergillus fumigatus* ATCC 58128, aa 26 (van Loon et al., 1997)

phyA gene from *Aspergillus fumigatus* ATCC 26906, aa 26 (van Loon et al., 1997)

phyA gene from *Aspergillus fumigatus* ATCC 32239, aa 30 (van Loon et al., 1997)

phyA gene from *Aspergillus nidulans*, aa 25 (Pasamontes et al., 1997a)

phyA gene from *Talaromyces thermophilus* ATCC 20186, aa 24 (Pasamontes et al., 1997a)

phyA gene from *Myceliophthora thermophila*, aa 19 (Mitchell et al., 1997)

Table 2 shows the homology of the phytase sequences mentioned above.

sequences, e. g. of the phytases from different *A. fumigatus* strains, dominate the calculated consensus sequence.

TABLE 1

| | |
|---|---|
| *Aspergillus terreus* 9A-1 phytase: | 0.50 |
| *Aspergillus terreus* cbs116.46 phytase: | 0.50 |
| *Aspergillus niger* var. awamori phytase: | 0.3333 |
| *Aspergillus niger* T213 phytase: | 0.3333 |
| *Aspergillus niger* NRRL3135 phytase: | 0.3333 |
| *Aspergillus fumigatus* ATCC 13073 phytase: | 0.20 |
| *Aspergillus fumigatus* ATCC 32722 phytase: | 0.20 |
| *Aspergillus fumigatus* ATCC 58128 phytase: | 0.20 |
| *Aspergillus fumigatus* ATCC 26906 phytase: | 0.20 |
| *Aspergillus fumigatus* ATCC 32239 phytase: | 0.20 |
| *Aspergillus nidulans* phytase: | 1.00 |
| *Talaromyces thermophilus* ATCC 20186 phytase: | 1.00 |
| *Myceliophthora thermophila* phytase: | 1.00 |

TABLE 2

| | % identity | | | | | | |
|---|---|---|---|---|---|---|---|
| | *A. terreus* 9A-1 | *A. terreus* cbs116.46 | *A. niger* NRRL 3135 | *A. fumigatus* 13073 | *A. nidulans* | *T. thermophilus* | *M. thermophila* |
| *A. terreus* 9A-1 | | 89.1 | 62.0 | 60.6 | 59.3 | 58.3 | 48.6 |
| *A. terreus* cbs | 90.7 | | 63.6 | 62.0 | 61.2 | 59.7 | 49.1 |
| *A. niger* NRRL 3135 | 67.3 | 68.9 | | 66.8 | 64.2 | 62.5 | 49.4 |
| *A. fumigatus* 13073 | 66.1 | 67.2 | 71.1 | | 68.0 | 62.6 | 53.0 |
| *A. nidulans* | 65.0 | 66.7 | 69.0 | 73.3 | | 60.5 | 52.5 |
| *T. thermophilus* | 63.8 | 64.5 | 68.9 | 68.1 | 67.4 | | 49.8 |
| *M. thermophila* | 53.7 | 54.6 | 57.6 | 61.0 | 59.9 | 57.8 | |
| | | | | % similarity | | | |

Table 2: Homology of the fungal phytases. The amino acid sequences of the phytases used in the alignment were compared by the program GAP (GCG program package, 9; Devereux et al., 1984) using the standard parameters. The comparison was restricted to the part of the sequence that was also used for the alignment (see legend to FIG. 1) lacking the signal peptide which was rather divergent. The numbers above and beneath the diagonal represent the amino acid identities and similarities, respectively.

EXAMPLE 2

Calculation of the Amino Acid Sequence of Fungal Consensus Phytases

Using the refined alignment of Example 1 as input, the consensus sequence was calculated by the program PRETTY from the Sequence Analysis Package Release 9.0 (Devereux et al., 1984). PRETTY prints sequences with their columns aligned and can display a consensus sequence for the alignment. A vote weight that pays regard to the similarity between the amino acid sequences of the phytases aligned were assigned to all sequences. The vote weight was set such as the combined impact of all phytases from one sequence subgroup (same species of origin but different strains), e. g. the amino acid sequences of all phytases from *A. fumigatus*, on the election was set one, that means that each sequence contributes with a value of 1 divided by the number of strain sequences (see Table 1). By this means, it was possible to prevent that very similar amino acid Table 1: Vote weights of the amino acid sequences of the fungal phytases used. The table shows the vote weights used to calculate the consensus sequence of the fungal phytases.

The program PRETTY was started with the following parameters: The plurality defining the number of votes below which there is no consensus was set on 2.0. The threshold, which determines the scoring matrix value below which an amino acid residue may not vote for a coalition of residues, was set on 2. PRETTY used the PrettyPep.Cmp consensus scoring matrix for peptides.

Ten positions of the alignment (position 46, 66, 82, 138, 162, 236, 276, 279, 280, 308; FIG. 1), for which the program was not able to determine a consensus residue, were filled by hand according to the following rules: if a most frequent residue existed, this residue was chosen (138, 236, 280); if a prevalent group of chemically similar or equivalent residues occurred, the most frequent or, if not available, one residues of this group was selected (46, 66, 82, 162, 276, 308). If there was either a prevalent residue nor a prevalent group, one of the occurring residues was chosen according to common assumption on their influence on the protein stability (279). Eight other positions (132, 170, 204, 211, 275, 317, 384, 447; FIG. 1) were not filled with the amino acid residue selected by the program but normally with amino acids that occur with the same frequency as the residues that were chosen by the program. In most cases, the slight underrating of the three *A. niger* sequences (sum of the vote weights: 0.99) was eliminated by this corrections.

Table 3 shows the homology of the calculated fungal consensus phytase amino acid sequence to the phytase sequences used for the calculation.

TABLE 3

| Phytase | Identity [%] | Similarity [%] |
| --- | --- | --- |
| A. niger T213 | 76.6 | 79.6 |
| A. niger var. awamori | 76.6 | 79.6 |
| A. niger NRRL3135 | 76.6 | 79.4 |
| A. nidulans | 77.4 | 81.5 |
| A. terreus 9A-1 | 70.7 | 74.8 |
| A. terreus cbs116.46 | 72.1 | 75.9 |
| A. fumigatus 13073 | 80.0 | 83.9 |
| A. fumigatus 32239 | 78.2 | 82.3 |
| T. thermophilus | 72.7 | 76.8 |
| M. thermophila | 58.3 | 64.5 |

Table 3: Homology of the amino acid sequence of fungal consensus phytase to the phytases used for its calculation. The amino acid sequences of all phytases were compared with the fungal consensus phytase sequence using the program GAP (GCG program package, 9.0). Again, the comparison was restricted to that part of the sequence that was used in the alignment.

EXAMPLE 3 (SEQ ID:9)

Conversion of the Fungal Consensus Phytase (SEQ ID:1) Amino Acid Sequence to a DNA Sequence The first 26 amino acid residues of A. terreus cbs116.46 phytase were used as signal peptide and, therefore, fused to the N-terminus of all consensus phytases. For this stretch, we used a special method to calculate the corresponding DNA sequence. Purvis et al. (1987) proposed that the incorporation of rare codons in a gene has an influence on the folding efficiency of the protein. Therefore, at least the distribution of rare codons in the signal sequence of A. terreus cbs116.46, which was used for the fungal consensus phytase and which is very important for secretion of the protein, but converted into the S. cerevisiae codon usage, was transferred into the new signal sequence generated for expression in S. cerevisiae. For the remaining parts of the protein, we used the codon frequency table of highly expressed S. cerevisiae genes, obtained from the GCG program package, to translate the calculated amino acid sequence into a DNA sequence. The resulting sequence of the fcp gene are shown in FIG. 2 (SEQ ID:4).

EXAMPLE 4

Construction and Cloning of the Fungal Consensus Phytase Genes

The calculated DNA sequence of fungal consensus phytase was divided into oligonucleotides of 85 bp, alternately using the sequence of the sense and the anti-sense strand. Every oligonucleotide overlaps 20 bp with its previous and its following oligonucleotide of the opposite strand. The location of all primers, purchased by Microsynth, Balgach (Switzerland) and obtained in a PAGE-purified form, is indicated in FIG. 2.

In three PCR reactions, the synthesized oligonucleotides were composed to the entire gene. For the PCR, the High Fidelity Kit from Boehringer Mannheim (Boehringer Mannheim, Mannheim, Germany) and the thermo cycler The Protokol™ from AMS Biotechnology (Europe) Ltd. (Lugano, Switzerland) were used.

Oligonucleotide CP-1 to CP-10 (Mix 1, FIG. 2) were mixed to a concentration of 0.2 pMol/µl per each oligonucleotide. A second oligonucleotide mixture (Mix 2) was prepared with CP-9 to CP-22 (0.2 pMol/µl per each oligonucleotide). Additionally, four short primers were used in the PCR reactions:

```
CP-a:           Eco RI
        5'-TAT ATG AAT TCA TGG GCG TGT TCG TC-3'  (SEQ.ID:5)

CP-b:
        5'-TGA AAA GTT CAT TGA AGG TTT C-3'  (SEQ ID:6)

CP-c:
        5'-TCT TCG AAA GCA GTA CAA GTA C-3'  (SEQ ID:7)

CP-e:           Eco RI
        5'-TAT ATG AAT TCT TAA GCG AAA C-3'  (SEQ ID:8)

PCR reaction a:  10 µl Mix 1 (2.0 pmol of each oligonucleotide)
                 2 µl nucleotides (10 mM each nucleotide)
                 2 µl primer CP-a (10 pmol/µl)
                 2 µl primer CP-c (10 pmol/µl)
                 10,0 µl PCR buffer
                 0.75 µl polymerase mixture
                 73.25 µl H2O PCR reaction b:  10 µl Mix 2 (2.o pmol of each oligonucleotide)
                 2 µl nucleotides (10 mM each nucleotide)
                 2 µl primer CP-b (10 pmol/µl)
                 2 µl primer CP-e (10 pmol/µl)
```

```
                  -continued
       10,0 µl PCR buffer 0.75 µl polymerase mixture (2.6 U)

73.25 µl H2O

Reaction conditions for PCR reaction a and b:

step 1    2 min - 45° C.

step 2    30 sec - 72° C.

step 3    30 sec - 94° C.

step 4    30 sec - 52° C.

step 5    1 min - 72° C.
```

Step 3 to 5 were repeated 40-times.

The PCR products (670 and 905 bp) were purified by an agarose gel electrophoresis (0.9% agarose) and a following gel extraction (QIAEX II Gel Extraction Kit, Qiagen, Hilden, Germany). The purified DNA fragments were used for the PCR reaction c.

| PCR reaction c: | 6 µl PCR product of reaction a (≈50 ng) |
| --- | --- |
| | 6 µl PCR product of reaction b (≈50 ng) |
| | 2 µl primer CP-a (10 pmol/µl) |
| | 2 µl primer CP-e (10 pmol/µl) |
| | 10,0 µl PCR buffer |
| | 0.75 µl polymerase mixture (2.6 U) |
| | 73.25 µl H2O |
| Reaction conditions for PCR reaction c: | |
| step 1 | 2 min - 94° C. |
| step 2 | 30 sec - 940° C. |
| step 3 | 30 sec - 55° C. |
| step 4 | 1 min - 72° C. |

Step 2 to 4 were repeated 31-times.

The resulting PCR product (1.4 kb) was purified as mentioned above, digested with Eco RI, and ligated in an Eco RI-digested and dephosphorylated pBsk(−)-vector (Stratagene, La Jolla, Calif., USA). 1 µl of the ligation mixture was used to transform *E. coli* XL-1 competent cells (Stratagene, La Jolla, Calif., USA). All standard procedures were carried out as described by Sambrook et al. (1987). The constructed fungal consensus phytase gene (fcp) was verified by sequencing (plasmid pBsk⁻-fcp).

EXAMPLE 5

Expression of the Fungal Consensus Phytase Gene fcp and Its Variants in *Saccharomyces cerevisiae* and Their Purification from Culture Supernatant A fungal consensus phytase gene (SEQ ID:4) was isolated from the plasmid pBsk⁻fcp ligated into the Eco RI sites of the expression cassette of the *Saccharomyces cerevisiae* expression vector pYES2 (Invitrogen, San Diego, Calif., USA) or subcloned between the shortened GAPFL (glyceraldhyde-3-phosphate dehydrogenase) promoter and the pho5 terminator as described by Janes et al. (1990). The correct orientation of the gene was checked by PCR. Transformation of *S. cerevisiae* strains. e. g. INVSc1 (Invitrogen, San Diego, Calif., USA) was done according to Hinnen et al. (1978). Single colonies harboring the phytase gene under the control of the GAPFL promoter were picked and cultivated in 5 ml selection medium (SD-uracil, Sherman et al., 1986) at 30° C. under vigorous shaking (250 rpm) for one day. The preculture was then added to 500 ml YPD medium (Sherman et al., 1986) and grown under the same conditions. Induction of the gal1 promoter was done according to manufacturer's instruction. After four days of incubation cell broth was centrifuged (7000 rpm, GS3 rotor, 15 min, 5° C.) to remove the cells and the supernatant was concentrated by way of ultrafiltration in Amicon 8400 cells (PM30 membranes) and ultrafree-15 centrifugal filter devices (Biomax-30K, Millipore, Bedford, Mass., USA). The concentrate (10 ml) was desalted on a 40 ml Sephadex G25 Superfine column (Pharmacia Biotech, Freiburg, Germany), with 10 mM sodium acetate, pH 5.0, serving as elution buffer. The desalted sample was brought to 2 M $(NH_4)_2SO_4$ and directly loaded onto a 1 ml Butyl Sepharose 4 Fast Flow hydrophobic interaction chromatography column (Pharmacia Biotech, Feiburg, Germany) which was eluted with a linear gradient from 2 M to 0 M $(NH_4)_2SO_4$ in 10 mM sodium acetate, pH 5.0. Phytase was eluted in the break-through, concentrated and loaded on a 120 ml Sephacryl S-300 gel permeation chromatography column (Pharmacia Biotech, Freiburg, Germany). Fungal consensus phytase and fungal consensus phytase 7 eluted as a homogeneous symmetrical peak and was shown by SDS-PAGE to be approx. 95% pure.

EXAMPLE 6

Expression of the Fungal Consensus Phytase Genes fcp and Its Variants in *Hansenula polymorpha*

The phytase expression vectors, used to transform *H. polymorpha*, was constructed by inserting the Eco RI fragment of pBsk⁻fcp encoding the consensus phytase or a variant into the multiple cloning site of the *H. polymorpha* expression vector pFPMT121, which is based on an ura3 selection marker and the FMD promoter. The 5' end of the fcp gene is fused to the FMD promoter, the 3' end to the MOX terminator (Gellissen et al., 1996; EP 0299 108 B). The resulting expression vector are designated pFPMTfcp and pBsk⁻fcp7.

The constructed plasmids were propagated in *E. coli*. Plasmid DNA was purified using standard state of the art procedures. The expression plasmids were transformed into the *H. polymorpha* strain RP11 deficient in orotidine-5'-phosphate decarboxylase (ura3) using the procedure for preparation of competent cells and for transformation of yeast as described in Gelissen et al. (1996). Each transformation mixture was plated on YNB (0.14% w/v Difco YNB and 0.5% ammonium sulfate) containing 2% glucose and 1.8% agar and incubated at 37° C. After 4 to 5 days individual transformant colonies were picked and grown in the liquid medium described above for 2 days at 37° C. Subsequently, an aliquot of this culture was used to inoculate fresh vials with YNB-medium containing 2% glucose. After seven further passages in selective medium, the expression vector integrates into the yeast genome in multimeric form. Subsequently, mitotically stable transformants were obtained by two additional cultivation steps in 3 ml non-selective liquid medium (YPD, 2% glucose, 10 g yeast extract, and 20 g peptone). In order to obtain genetically homogeneous recombinant strains an aliquot from the last stabilization culture was plated on a selective plate. Single colonies were isolated for analysis of phytase expression in YNB containing 2% glycerol instead of glucose to derepress the fmd promoter. Purification of the fungal consensus phytases was done as described in Example 5.

EXAMPLE 7

Expression of the Fungal Consensus Genes fcp and Its Variants in *Aspergillus niger*

Plasmid pBsk⁻fcp or the corresponding plasmid of a variant of the fcp gene were used as template for the introduction of a Bsp HI-site upstream of the start codon of the genes and an Eco RV-site downstream of the stop codon. The Expand™ High Fidelity PCR Kit (Boehringer Mannheim, Mannheim, Germany) was used with the following primers:

Primer Asp-1: Bsp HI

5'-TAT ATC ATG AGC GTG TTC GTC GTG CTA CTG TTC-3' (SEQ ID:9)

Primer Asp-2 for cloning of fcp and fcp7:

3'-ACC CGA CTT ACA AAG CGA ATT CTA TAG ATA TAT-5' (SEQ ID:10)

Eco RV

The reaction was performed as described by the supplier. The PCR-amplified fcp gene had a new Bsp HI site at the start codon, introduced by primer Asp-1, which resulted in a replacement of the second amino acid residue glycine by serine. Subsequently, the DNA-fragment was digested with Bsp HI and Eco RV and ligated into the Nco I site downstream of the glucoamylase promoter of *Aspergillus niger* (glaA) and the Eco RV site upstream of the *Aspergillus nidulans* tryptophan C terminator (trpC) (Mullaney et al., 1985). After this cloning step, the genes were sequenced to detect possible failures introduced by PCR. The resulting expression plasmids which basically corresponds to the pGLAC vector as described in Example 9 of EP 684 313, contained the orotidine-5'-phosphate decarboxylase gene (pyr4) of *Neurospora crassa* as a selection marker. Transformation of *Aspergillus niger* and expression of the consensus phytase genes was done as described in EP 684 313. The fungal consensus phytases were purified as described in Example 5.

EXAMPLE 8

Construction of Muteins of Fungal Consensus Phytase

To construct muteins for expression in *A. niger*, *S. cerevisiae*, or *H. polymorpha*, the corresponding expression plasmid containing the fungal consensus phytase gene was used as template for site-directed mutagenesis. Mutations were introduced using the "quick exchange™ site-directed mutagenesis kit" from Stratagene (La Jolla, Calif., USA) following the manufacturer's protocol and using the corresponding primers. All mutations made and the corresponding primers are summarized in Table 4. Clones harboring the desired mutation were identified by DNA sequence analysis as known in the art. The mutated phytase were verified by sequencing of the complete gene.

TABLE 4

| mutation | Primer set | |
|---|---|---|
| | Ssp BI | |
| Q50L | 5'-CAC TTG TGG GGT TTG TAC AGT CCA TAC TTC TC-3' | (SEQ ID:11) |
| | 5'-GAG AAG TAT GGA CTG TAC AAA CCC CAC AAG TG-3' | (SEQ ID:12) |
| | Kpn I | |
| Q50T | 5'-CAC TTG TGG GGT ACC TAC TCT CCA TAC TTC TC-3' | (SEQ ID:13) |
| | 5'-GA GAA GTA TGG AGA GTA GGT ACC CCA CAA GTG-3' | (SEQ ID:14) |
| Q50G | 5'-CAC TTG TGG GGT GGT TAC TCT CCA TAC TTC TC-3' | (SEQ ID:15) |
| | 5'-GA GAA GTA TGG AGA GTA ACC ACC CCA CAA GTG-3' | (SEQ ID:16) |
| | Kpn I | |
| Q50T-Y51N | 5'-CAC TTG TGG GGT ACC AAC TCT CCA TAC TTC TC-3' | (SEQ ID:17) |
| | 5'-GA GAA GTA TGG AGA GTT GGT ACC CCA CAA GTG-3' | (SEQ ID:18) |
| | Bsa I | |
| Q50L-Y51N | 5'-CAC TTG TGG GGT CTC AAC TCT CCA TAC TTC TC-3' | (SEQ ID:19) |
| | 5'-GA GAA GTA TGG AGA GTT GAG ACC CCA CAA GTG-3' | (SEQ ID:20) |

Table 4: Primers used for the introduction of single mutations into fungal consensus phytase. For the introduction of each mutation, two primers containing the desired mutation were required (see Example 8). The changed triplets are highlighted in bold letters.

EXAMPLE 9

Determination of the Phytase Activity and of the Temperature Optimum of the Consensus Phytase and Its Variants Phytase activity was determined basically as described by Mitchell et al. (1997). The activity was measured in a assay mixture containing 0.5% phytic acid (≈5 mM), 200 mM sodium acetate, pH 5.0. After 15 min incubation at 37° C., the reaction was stopped by addition of an equal volume of 15% trichloroacetic acid. The liberated phosphate was quantified by mixing 100 μl of the assay mixture with 900 μl H$_2$O and 1 ml Of 0.6 M H$_2$SO$_4$, 2% ascorbic acid and 0.5% ammonium molybdate. Standard solutions of potassium phosphate were used as reference. One unit of enzyme activity was defined as the amount of enzyme that releases 1 μmol phosphate per minute at 37° C. The protein concentration was determined using the enzyme extinction coefficient at 280 nm calculated according to Pace et al. (1995): fungal consensus phytase, 1.101; fungal consensus phytase 7, 1.068. In case of pH-optimum curves, purified enzymes were diluted in 10 mM sodium acetate, pH 5.0. Incubations were started by mixing aliquots of the diluted protein with an equal volume of 1% phytic acid (≈10 mM) in a series of different buffers: 0.4 M glycine/HCl, pH 2.5; 0.4 M acetate/NaOH, pH 3.0, 3.5, 4.0, 4.5, 5.0, 5.5; 0.4 M imidazole/HCl, pH 6.0, 6.5; 0.4 M Tris/HCl pH 7.0, 7.5, 8.0, 8.5, 9.0. Control experiments showed that pH was only slightly affected by the mixing step. Incubations were performed for 15 min at 37° C. as described above.

For determination of the substrate specificities of the phytases, phytic acid in the assay mixture was replaced by 5 mM concentrations of the respective phosphate compounds. The activity tests were performed as described above.

For determination of the temperature optimum, enzyme (100 μl) and substrate solution (100 μl) were pre-incubated for 5 min at the given temperature. The reaction was started by addition of the substrate solution to the enzyme. After 15 min incubation, the reaction was stopped with trichloroacetic acid and the amount of phosphate released was determined.

Figure 4A:
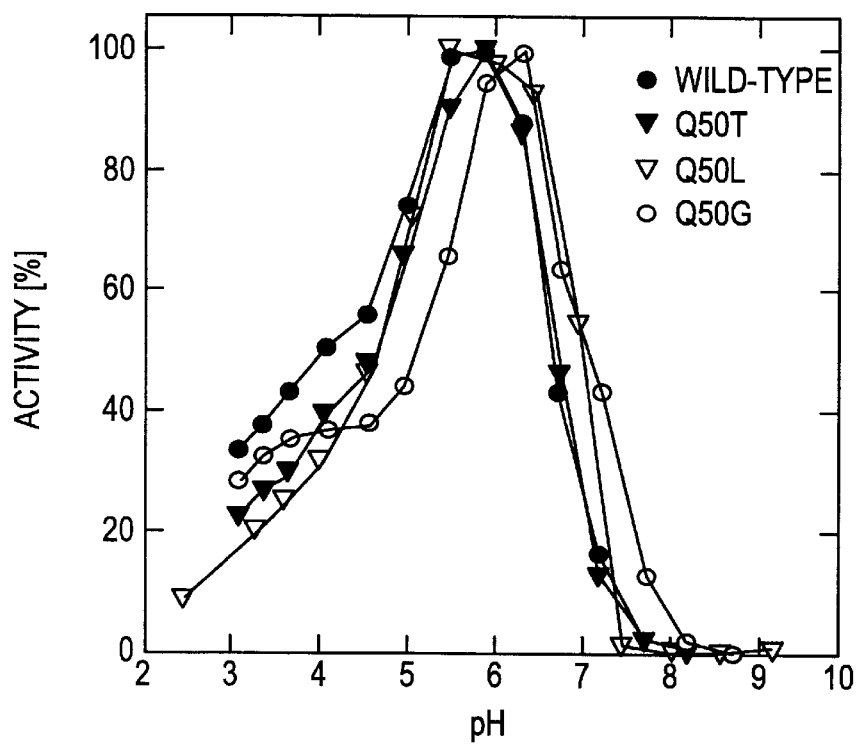
Figure 4B:
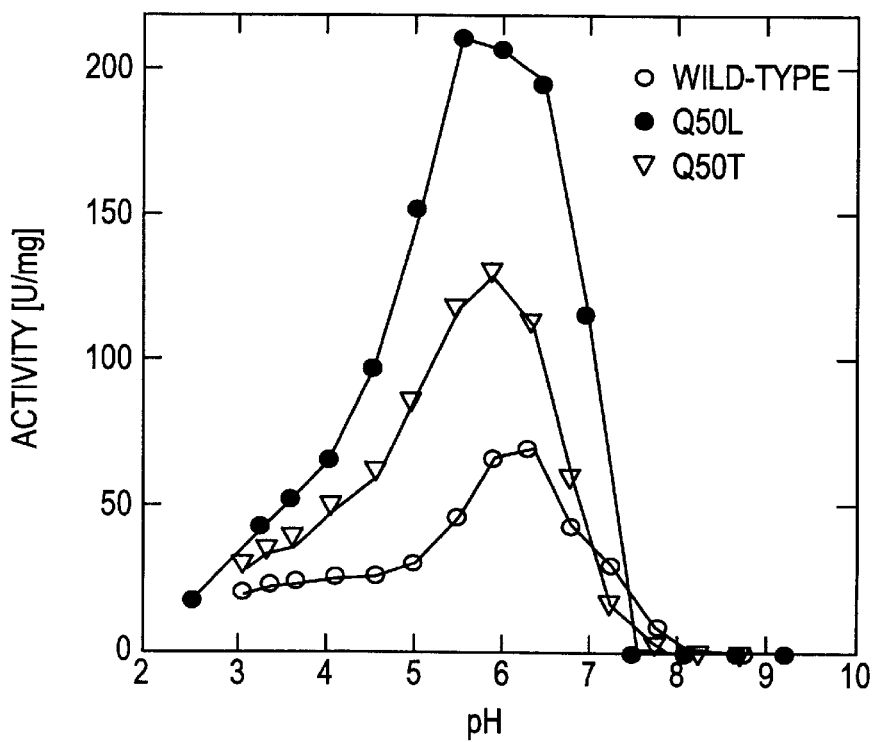
Figure 5A:
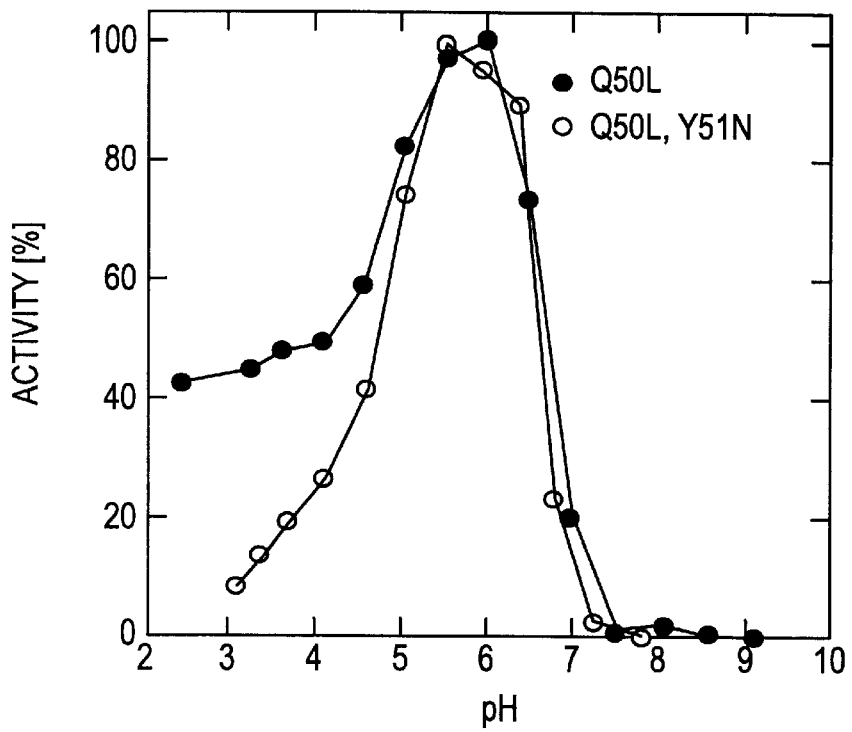
Figure 5B:
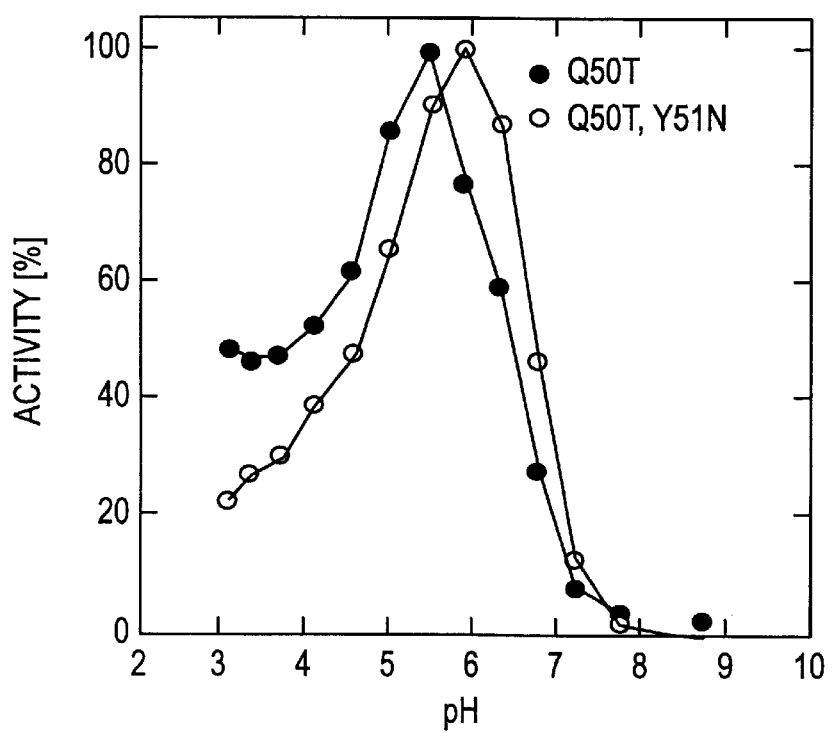
Figure 6:
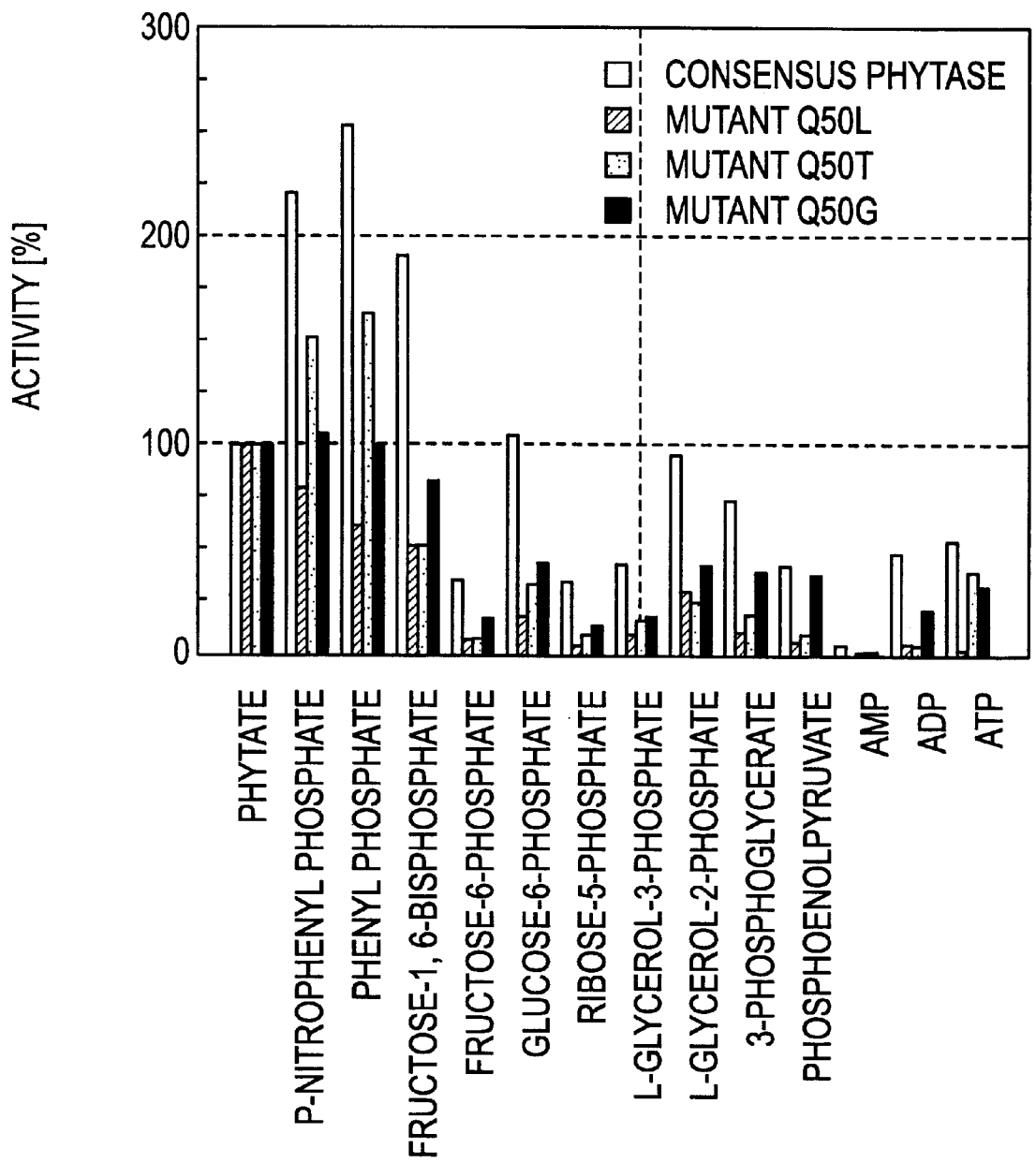

The pH-optimum of the original fungal consensus phytase was around pH 6.0–6.5 (70 U/mg). By introduction of the Q50T mutation, the pH-optimum shifted to pH 6.0 (130 U/mg), while the replacement by a leucine at the same position resulted in a maximum activity around pH 5.5 (212 U/mg). The exchange Q50G resulted in a pH-optimum of the activity above pH 6.0 (see FIG. 4). The exchange of tyrosine at position 51 with asparagine resulted in a relative increase of the activity below pH 5.0 (see FIG. 5). Especially by the Q50L mutation, the specificity for phytate of fungal consensus phytase was drastically increased (see FIG. 6).

The temperature optimum of fungal consensus phytase (70° C.) was 15–25° C. higher than the temperature optimum of the wild-type phytases (45–55° C.) which were used to calculate the consensus sequence (see Table 5 and FIG. 3).

TABLE 5

| phytase | temperature optimum | Tm[a] |
|---|---|---|
| Consensus phytase | 70° C. | 78.0° C. |
| A. niger NRRL3135 | 55° C. | 63.3° C. |
| A. fumigatus 13073 | 55° C. | 62.5° C. |
| A. terreus 9A-1 | 49° C. | 57.5° C. |
| A. terreus cbs | 45° C. | 58.5° C. |
| A. nidulans | 45° C. | 55.7° C. |
| M. thermophila | 55° C. | — |

Figure 7A:
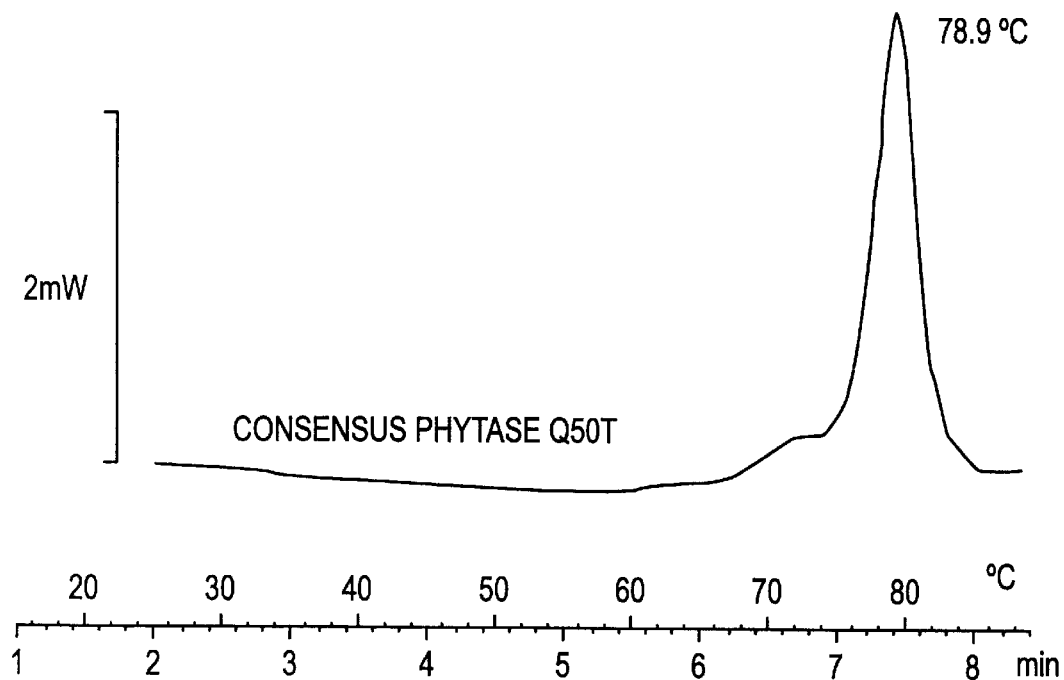
Figure 7B:
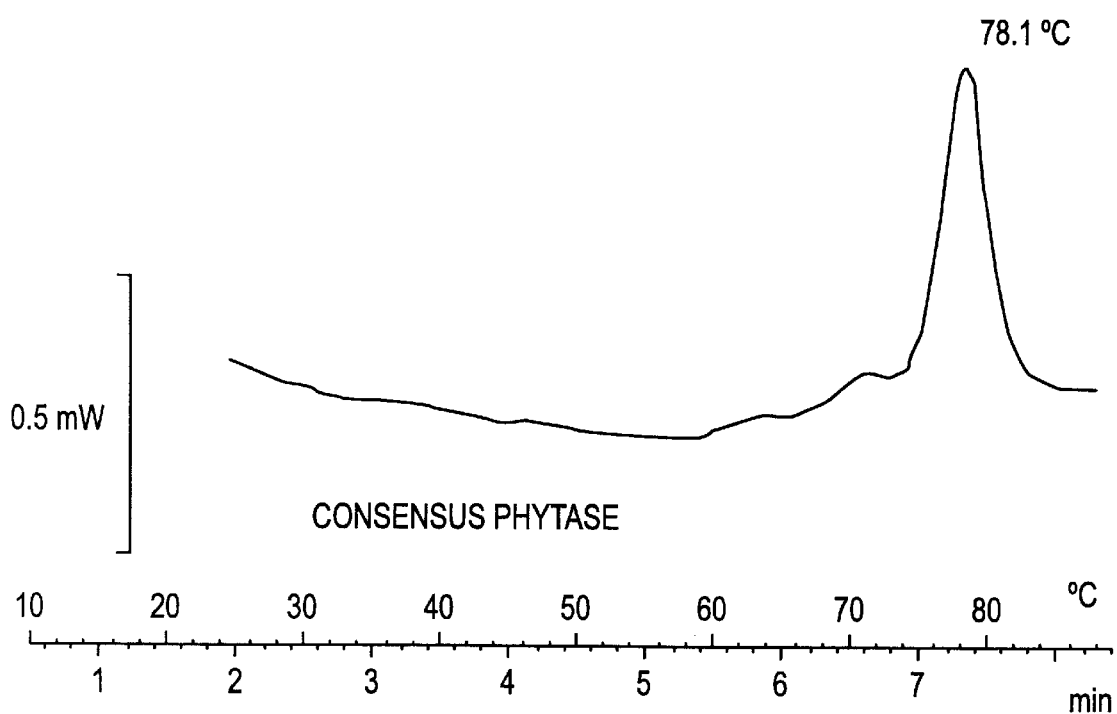

[a]The T$_m$-values were determined by differential scanning calorimetry as described in Example 10 and shown in FIG. 7.

Table 5: Temperature optimum and T$_m$-value of fungal consensus phytase and of the phytases from A. fumigatus, A. niger, A. nidulans, and M. thermophila. The temperature optima were taken from FIG. 3.

EXAMPLE 10

Determination of the Melting Point by Differential Scanning Calorimetry (DSC)

In order to determine the unfolding temperature of the fungal consensus phytases, differential scanning calorimetry was applied as previously published by Brugger et al. (1997). Solutions of 50–60 mg/ml homogeneous phytase were used for the tests. A constant heating rate of 10° C./min was applied up to 90° C.

The determined melting points clearly show the strongly improved thermostability of the fungal consensus phytase in comparison to the wild-type phytases (see Table 5 and FIG. 7). FIG. 7 shows the melting profile of fungal consensus phytase and its mutant Q50T. Its common melting point was determined between 78 to 79° C.

What is claimed is:

1. A consensus protein which has the amino acid sequence selected from the group consisting of SEQ ID NO:1 and amino acid sequences containing amino acid additions, deletions, and replacements to SEQ ID NO:1, which sequences have up to two amino acids which are different from the sequence of SEQ ID NO:1.

2. A polypeptide having the amino acid sequence of SEQ ID NO:1.

3. A consensus protein which has the amino acid sequence selected from the group consisting of SEQ ID NO:2 and amino acid sequences containing amino acid additions, deletions, and replacements to SEQ ID NO:2, which sequences have up to two amino acids which are different from the sequence of SEQ ID NO:2.

4. A mutein which has the amino acid sequence of SEQ ID NO:2 with the proviso that Q at position 50 is replaced by L, T or G.

5. A mutein which has the amino acid sequence of SEQ ID NO:2 with the proviso that Q at position 50 is replaced by T and, Y at position 51 is replaced by N.

6. A mutein which has the amino acid sequence of SEQ ID NO:2 with the proviso that Q at position 50 is replaced by L and, Y at position 51 is replaced by N.

7. A polypeptide having the amino acid sequence of SEQ ID NO:2.

8. A food composition comprising a food in combination with an amino acid sequence selected from the group consisting of SEQ ID NO:1 and amino acid sequences containing amino acid additions, deletions, and replacements to SEQ ID NO:1, which sequences have up to two amino acids which are different from the sequence of SEQ ID NO:1.

9. A food composition according to claim 8 comprising a polypeptide having the amino acid sequence of SEQ ID NO:1.

10. A food composition comprising a food in combination with an amino acid sequence selected from the group consisting of SEQ ID NO:2 and amino acid sequences containing amino acid additions, deletions, and replacements to SEQ ID NO:2, which sequences have up to two amino acids which are different from the sequence of SEQ ID NO:2.

11. A food composition according to claim 10 comprising a polypeptide having the amino acid sequence of SEQ ID NO:2.

* * * * *

SEQUENCE LISTING

<160> NUMBER OF SEQ ID NOS: 20

<210> SEQ ID NO 1
<211> LENGTH: 441
<212> TYPE: PRT
<213> ORGANISM: Artificial Sequence
<220> FEATURE:
<223> OTHER INFORMATION: Description of Artificial Sequence:consensus
      sequence

<400> SEQUENCE: 1

Asn Ser His Ser Cys Asp Thr Val Asp Gly Gly Tyr Gln Cys Phe Pro
 1               5                  10                  15

Glu Ile Ser His Leu Trp Gly Gln Tyr Ser Pro Tyr Phe Ser Leu Glu
            20                  25                  30

Asp Glu Ser Ala Ile Ser Pro Asp Val Pro Asp Cys Arg Val Thr
        35                  40                  45

Phe Val Gln Val Leu Ser Arg His Gly Ala Arg Tyr Pro Thr Ser Ser
    50                  55                  60

```
Lys Ser Lys Ala Tyr Ser Ala Leu Ile Glu Ala Ile Gln Lys Asn Ala
 65                  70                  75                  80

Thr Ala Phe Lys Gly Lys Tyr Ala Phe Leu Lys Thr Tyr Asn Tyr Thr
             85                  90                  95

Leu Gly Ala Asp Asp Leu Thr Pro Phe Gly Glu Asn Gln Met Val Asn
            100                 105                 110

Ser Gly Ile Lys Phe Tyr Arg Arg Tyr Lys Ala Leu Ala Arg Lys Ile
        115                 120                 125

Val Pro Phe Ile Arg Ala Ser Gly Ser Asp Arg Val Ile Ala Ser Ala
130                 135                 140

Glu Lys Phe Ile Glu Gly Phe Gln Ser Ala Lys Leu Ala Asp Pro Gly
145                 150                 155                 160

Ser Gln Pro His Gln Ala Ser Pro Val Ile Asp Val Ile Ile Pro Glu
                165                 170                 175

Gly Ser Gly Tyr Asn Asn Thr Leu Asp His Gly Thr Cys Thr Ala Phe
            180                 185                 190

Glu Asp Ser Glu Leu Gly Asp Asp Val Glu Ala Asn Phe Thr Ala Leu
        195                 200                 205

Phe Ala Pro Ala Ile Arg Ala Arg Leu Glu Ala Asp Leu Pro Gly Val
210                 215                 220

Thr Leu Thr Asp Glu Asp Val Val Tyr Leu Met Asp Met Cys Pro Phe
225                 230                 235                 240

Glu Thr Val Ala Arg Thr Ser Asp Ala Thr Glu Leu Ser Pro Phe Cys
                245                 250                 255

Ala Leu Phe Thr His Asp Glu Trp Arg Gln Tyr Asp Tyr Leu Gln Ser
            260                 265                 270

Leu Gly Lys Tyr Tyr Gly Tyr Gly Ala Gly Asn Pro Leu Gly Pro Ala
        275                 280                 285

Gln Gly Val Gly Phe Ala Asn Glu Leu Ile Ala Arg Leu Thr Arg Ser
290                 295                 300

Pro Val Gln Asp His Thr Ser Thr Asn His Thr Leu Asp Ser Asn Pro
305                 310                 315                 320

Ala Thr Phe Pro Leu Asn Ala Thr Leu Tyr Ala Asp Phe Ser His Asp
                325                 330                 335

Asn Ser Met Ile Ser Ile Phe Ala Leu Gly Leu Tyr Asn Gly Thr
            340                 345                 350

Ala Pro Leu Ser Thr Thr Ser Val Glu Ser Ile Glu Glu Thr Asp Gly
        355                 360                 365

Tyr Ser Ala Ser Trp Thr Val Pro Phe Gly Ala Arg Ala Tyr Val Glu
370                 375                 380

Met Met Gln Cys Gln Ala Glu Lys Glu Pro Leu Val Arg Val Leu Val
385                 390                 395                 400

Asn Asp Arg Val Val Pro Leu His Gly Cys Ala Val Asp Lys Leu Gly
                405                 410                 415

Arg Cys Lys Arg Asp Asp Phe Val Glu Gly Leu Ser Phe Ala Arg Ser
            420                 425                 430

Gly Gly Asn Trp Ala Glu Cys Phe Ala
        435                 440

<210> SEQ ID NO 2
<211> LENGTH: 467
<212> TYPE: PRT
<213> ORGANISM: Artificial Sequence
<220> FEATURE:
```

-continued

<223> OTHER INFORMATION: Description of Artificial Sequence:consensus
       sequence

<400> SEQUENCE: 2

```
Met Gly Val Phe Val Leu Leu Ser Ile Ala Thr Leu Phe Gly Ser
 1               5                  10                  15

Thr Ser Gly Thr Ala Leu Gly Pro Arg Gly Asn Ser His Ser Cys Asp
            20                  25                  30

Thr Val Asp Gly Gly Tyr Gln Cys Phe Pro Glu Ile Ser His Leu Trp
        35                  40                  45

Gly Gln Tyr Ser Pro Tyr Phe Ser Leu Glu Asp Glu Ser Ala Ile Ser
    50                  55                  60

Pro Asp Val Pro Asp Asp Cys Arg Val Thr Phe Val Gln Val Leu Ser
65                  70                  75                  80

Arg His Gly Ala Arg Tyr Pro Thr Ser Ser Lys Ser Lys Ala Tyr Ser
                85                  90                  95

Ala Thr Tyr Asn Tyr Thr Leu Gly Ala Asp Asp Leu Thr Pro Phe Gly
            100                 105                 110

Glu Asn Gln Met Val Asn Ser Gly Ile Lys Phe Tyr Arg Arg Tyr Lys
        115                 120                 125

Ala Leu Ala Arg Lys Ile Val Pro Phe Ile Arg Ala Ser Gly Ser Asp
    130                 135                 140

Arg Val Ile Ala Ser Ala Glu Lys Phe Ile Glu Gly Phe Gln Ser Ala
145                 150                 155                 160

Lys Leu Ala Asp Pro Gly Ser Gln Pro His Gln Ala Ser Pro Val Ile
                165                 170                 175

Asp Leu Ile Glu Ala Ile Gln Lys Asn Ala Thr Ala Phe Lys Gly Lys
            180                 185                 190

Tyr Ala Phe Leu Lys Val Ile Ile Pro Glu Gly Ser Gly Tyr Asn Asn
        195                 200                 205

Thr Leu Asp His Gly Thr Cys Thr Ala Phe Glu Asp Ser Glu Leu Gly
    210                 215                 220

Asp Asp Val Glu Ala Asn Phe Thr Ala Leu Phe Ala Pro Ala Ile Arg
225                 230                 235                 240

Ala Arg Leu Glu Ala Asp Leu Pro Gly Val Thr Leu Thr Asp Glu Asp
                245                 250                 255

Val Val Tyr Leu Met Asp Met Cys Pro Phe Glu Thr Val Ala Arg Thr
            260                 265                 270

Ser Asp Ala Thr Glu Leu Ser Pro Phe Cys Ala Leu Phe Thr His Asp
        275                 280                 285

Glu Trp Arg Gln Tyr Asp Tyr Leu Gln Ser Leu Gly Lys Tyr Tyr Gly
    290                 295                 300

Tyr Gly Ala Gly Asn Pro Leu Gly Pro Ala Gln Gly Val Gly Phe Ala
305                 310                 315                 320

Asn Glu Leu Ile Ala Arg Leu Thr Arg Ser Pro Val Gln Asp His Thr
                325                 330                 335

Ser Thr Asn His Thr Leu Asp Ser Asn Pro Ala Thr Phe Pro Leu Asn
            340                 345                 350

Ala Thr Leu Tyr Ala Asp Phe Ser His Asp Asn Ser Met Ile Ser Ile
        355                 360                 365

Phe Phe Ala Leu Gly Leu Tyr Asn Gly Thr Ala Pro Leu Ser Thr Thr
    370                 375                 380

Ser Val Glu Ser Ile Glu Glu Thr Asp Gly Tyr Ser Ala Ser Trp Thr
385                 390                 395                 400
```

```
Val Pro Phe Gly Ala Arg Ala Tyr Val Glu Met Met Gln Cys Gln Ala
                405                 410                 415

Glu Lys Glu Pro Leu Val Arg Val Leu Val Asn Asp Arg Val Val Pro
            420                 425                 430

Leu His Gly Cys Ala Val Asp Lys Leu Gly Arg Cys Lys Arg Asp Asp
        435                 440                 445

Phe Val Glu Gly Leu Ser Phe Ala Arg Ser Gly Asn Trp Ala Glu
    450                 455                 460

Cys Phe Ala
465

<210> SEQ ID NO 3
<211> LENGTH: 1426
<212> TYPE: DNA
<213> ORGANISM: Artificial Sequence
<220> FEATURE:
<223> OTHER INFORMATION: Description of Artificial Sequence:consensus
      sequence

<400> SEQUENCE: 3
tatatgaatt catgggcgtg ttcgtcgtgc tactgtccat tgccaccttg ttcggttcca      60
catccggtac cgccttgggt cctcgtggta attctcactc ttgtgacact gttgacggtg    120
gttaccaatg tttcccagaa atttctcact tgtggggtca atactctcca tacttctctt    180
tggaagacga atctgctatt tctccagacg ttccagacga ctgtagagtt actttcgttc    240
aagttttgtc tagacacggt gctagatacc caacttcttc taagtctaag gcttactctg    300
ctttgattga agctattcaa aagaacgcta ctgctttcaa gggtaagtac gctttcttga    360
agacttacaa ctacactttg ggtgctgacg acttgactcc attcggtgaa aaccaaatgg    420
ttaactctgg tattaagttc tacagaagat acaaggcttt ggctagaaag attgttccat    480
tcattagagc ttctggttct gacagagtta ttgcttctgc tgaaaagttc attgaaggtt    540
ccaatctgc taagttggct gacccaggtt ctcaaccaca ccaagcttct ccagttattg    600
acgttattat tccagaagga tccggttaca acaacacttt ggaccacggt acttgtactg    660
ctttcgaaga ctctgaattg ggtgacgacg ttgaagctaa cttcactgct ttgttcgctc    720
cagctattag agctagattg gaagctgact tgccaggtgt tactttgact gacgaagacg    780
ttgtttactt gatggacatg tgtccattcg aaactgttgc tagaacttct gacgctactg    840
aattgtctcc attctgtgct tgttcactc acgacgaatg gagacaatac gactacttgc    900
aatctttggg taagtactac ggttacggtg ctggtaaccc attgggtcca gctcaaggtg    960
ttggtttcgc taacgaattg attgctagat tgactagatc tccagttcaa gaccacactt   1020
ctactaacca cactttggac tctaacccag ctactttccc attgaacgct actttgtacg   1080
ctgacttctc tcacgacaac tctatgattt ctatttctt cgctttgggt ttgtacaacg   1140
gtactgctcc attgtctact acttctgttg aatctattga agaaactgac ggttactctg   1200
cttcttggac tgttccattc ggtgctagag cttacgttga aatgatgcaa tgtcaagctg   1260
aaaaggaacc attggttaga gttttggtta acgacagagt tgttccattg cacggttgtg   1320
ctgttgacaa gttgggtaga tgtaagagag acgacttcgt tgaaggtttg tctttcgcta   1380
gatctggtgg taactgggct gaatgtttcg cttaagaatt catata              1426

<210> SEQ ID NO 4
<211> LENGTH: 1426
<212> TYPE: DNA
```

```
<213> ORGANISM: Artificial Sequence
<220> FEATURE:
<223> OTHER INFORMATION: Description of Artificial Sequence:consensus
      sequence

<400> SEQUENCE: 4
atatacttaa gtacccgcac aagcagcacg atgacaggta acggtggaac aagccaaggt      60
gtaggccatg gcggaaccca ggagcaccat taagagtgag aacactgtga caactgccac     120
caatggttac aaagggtctt taagagtga acaccccagt tatgagaggt atgaagagaa      180
accttctgct tagacgataa agaggtctgc aaggtctgct gacatctcaa tgaaagcaag     240
ttcaaaacag atctgtgcca cgatctatgg gttgaagaag attcagattc cgaatgagac     300
gaaactaact tcgataagtt ttcttgcgat gacgaaagtt cccattcatg cgaaagaact     360
tctgaatgtt gatgtgaaac ccacgactgc tgaactgagg taagccactt ttggtttacc     420
aattgagacc ataattcaag atgtcttcta tgttccgaaa ccgatctttc taacaaggta     480
agtaatctcg aagaccaaga ctgtctcaat aacgaagacg acttttcaag taacttccaa     540
aggttagacg attcaaccga ctgggtccaa gagttggtgt ggttcgaaga ggtcaataac     600
tgcaataata aggtcttcct aggccaatgt tgttgtgaaa cctggtgcca tgaacatgac     660
gaaagcttct gagacttaac ccactgctgc aacttcgatt gaagtgacga aacaagcgag     720
gtcgataatc tcgatctaac cttcgactga acggtccaca atgaaactga ctgcttctgc     780
aacaaatgaa ctacctgtac acaggtaagc tttgacaacg atcttgaaga ctgcgatgac     840
ttaacagagg taagacacga aacaagtgag tgctgcttac ctctgttatg ctgatgaacg     900
ttagaaaccc attcatgatg ccaatgccac gaccattggg taacccaggt cgagttccac     960
aaccaaagcg attgcttaac taacgatcta actgatctag aggtcaagtt ctggtgtgaa    1020
gatgattggt gtgaaacctg agattgggtc gatgaaaggg taacttgcga tgaaacatgc    1080
gactgaagag agtgctgttg agatactaaa gataaaagaa gcgaaaccca aacatgttgc    1140
catgacgagg taacagatga tgaagacaac ttagataact tctttgactg ccaatgagac    1200
gaagaacctg acaaggtaag ccacgatctc gaatgcaact ttactacgtt acagttcgac    1260
ttttccttgg taaccaatct caaaaccaat tgctgtctca acaaggtaac gtgccaacac    1320
gacaactgtt caacccatct acattctctc tgctgaagca acttccaaac agaaagcgat    1380
ctagaccacc attgacccga cttacaaagc gaattcttaa gtatat                   1426

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 5
tatatgaatt catgggcgtg ttcgtc                                           26

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 6
tgaaaagttc attgaaggtt tc                                               22
```

-continued

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 7
tgaaaagttc attgaaggtt tc                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 8
tgaaaagttc attgaaggtt tc                                              22

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 9
tatatcatga gcgtgttcgt cgtgctactg ttc                                  33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 10
acccgactta caaagcgaat tctatagata tat                                  33

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 11
cacttgtggg gtttgtacag tccatacttc tc                                   32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 12
gagaagtatg gactgtacaa accccacaag tg                                   32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 13
cacttgtggg gtacctactc tccatacttc tc                                        32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 14
gagaagtatg gagagtaggt accccacaag tg                                        32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 15
cacttgtggg gtggttactc tccatacttc tc                                        32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 16
gagaagtatg gagagtaacc accccacaag tg                                        32

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 17
cacttgtggg gtaccaactc tccatacttc tc                                        32

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 18
gagaagtatg gagagttggt accccacaag tg                                        32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 19
cacttgtggg gtctcaactc tccatacttc tc                                        32

<210> SEQ ID NO 20

```
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 20
gagaagtatg gagagttgag accccacaag tg                                32
```